United States Patent
Wakai

(10) Patent No.: US 9,383,596 B2
(45) Date of Patent: Jul. 5, 2016

(54) VARIABLE SPECTRUM ELEMENT

(71) Applicant: OLYMPUS CORPORATION, Tokyo (JP)

(72) Inventor: Hiroshi Wakai, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 372 days.

(21) Appl. No.: 13/955,658

(22) Filed: Jul. 31, 2013

(65) Prior Publication Data

US 2014/0036344 A1    Feb. 6, 2014

Related U.S. Application Data

(63) Continuation of application No. PCT/JP2012/051858, filed on Jan. 27, 2012.

(30) Foreign Application Priority Data

Feb. 1, 2011  (JP) ................. 2011-019706

(51) Int. Cl.
    *G02B 26/00*    (2006.01)
    *G02F 1/01*     (2006.01)
    (Continued)

(52) U.S. Cl.
    CPC .............. *G02F 1/0121* (2013.01); *G01J 3/26* (2013.01); *G02B 26/001* (2013.01); *A61B 1/00186* (2013.01)

(58) Field of Classification Search
    CPC ............ G02B 26/0833; G02B 26/001; G02B 26/0841; G02B 26/02; G02B 26/06
    USPC ......................................... 359/291, 578, 579
    See application file for complete search history.

(56) References Cited

U.S. PATENT DOCUMENTS

| 7,190,523 B2 * | 3/2007 | Yoda .................. G02B 6/29395 359/579 |
| 8,081,314 B2 * | 12/2011 | Kamihara ................ G01J 3/02 356/454 |
| 8,319,169 B2 * | 11/2012 | Funasaka ................. G02B 5/28 250/216 |

(Continued)

FOREIGN PATENT DOCUMENTS

| JP | 6-241899 A    | 9/1994 |
| JP | 2008-129149 A | 6/2008 |

(Continued)

OTHER PUBLICATIONS

International Search Report dated Feb. 28, 2012 issued in PCT/JP2012/051858.

*Primary Examiner* — Bumsuk Won
*Assistant Examiner* — Tamara Y Washington
(74) *Attorney, Agent, or Firm* — Scully, Scott, Murphy & Presser, P.C.

(57) ABSTRACT

A variable spectrum element includes: first and third sensors which are placed at positions at which the first and third sensors are symmetrical with respect to a line connecting the centers of mass of the surfaces of a pair of optical substrates opposite to each other, respectively; second and fourth sensors which are placed at positions at which the second and fourth sensors are symmetrical with respect to the line connecting the centers of mass, respectively; and first to fourth actuators which are placed on lines running from the center of mass of the surface of each of the pair of the optical substrates opposite to each other to the centers of the first to fourth sensors respectively, respectively.

14 Claims, 12 Drawing Sheets

(51) Int. Cl.
*G01J 3/26* (2006.01)
*A61B 1/00* (2006.01)

(56) References Cited

U.S. PATENT DOCUMENTS

| | | | |
|---|---|---|---|
| 8,482,737 B2 * | 7/2013 | Wakai | G01B 7/003 |
| | | | 356/454 |
| 2010/0027010 A1 * | 2/2010 | Matsumoto | G02B 26/001 |
| | | | 356/416 |
| 2010/0103522 A1 * | 4/2010 | Matsumoto | G01J 3/26 |
| | | | 359/578 |
| 2013/0010285 A1 * | 1/2013 | Wakai | G01B 7/003 |
| | | | 356/72 |

FOREIGN PATENT DOCUMENTS

| | | |
|---|---|---|
| JP | 2008-151544 A | 7/2008 |
| JP | 2010-224011 A | 10/2010 |
| JP | 2011-209574 A | 10/2011 |

\* cited by examiner

VARIABLE SPECTRUM ELEMENT

This application claims benefits of Japanese Patent Application No. 2011-019706 filed in Japan on Feb. 1, 2011, the contents of which are hereby incorporated by reference.

BACKGROUND OF THE INVENTION

1. Field of the Invention

This invention relates to a variable spectrum element.

2. Description of the Related Art

Variable spectrum elements each including an etalon device and a control unit have been known up to now as a variable spectrum element in which one of or both of a pair of optical substrates arranged opposite at a distance from each other are moved by an actuator like a piezoelectric device so that a distance between the surfaces of the optical substrates opposite to each other or a distance between the reflective films formed on the surfaces of the optical substrates opposite to each other (which is collectively called "surface distance between the optical substrates" hereinafter) is changed, with the result that optical characteristics of the variable spectrum element can be varied. (For example, refer to Japanese Patent TOKUKAI NO. 2008-129149.)

Also, it is known that such variable spectrum elements include a variable spectrum element in which: capacitive sensors for measuring a surface distance between the optical substrates are arranged on the surfaces of the optical substrates opposite to each other respectively in order to make the optical substrates have a desired surface distance; the current surface distance between the optical substrates is measured by the capacitive sensors with a predetermined sampling period; the measured surface distance between the optical substrates is compared with a desired surface distance between the optical substrates; and an actuator is made to operate on the basis of the result of the comparison between the measured surface distance and the desired surface distance so that the surface distance between the optical substrates is adjusted. (For example, refer to Japanese Patent TOKUKAI NO. Hei 6-241899.)

SUMMARY OF INVENTION

A variable spectrum element according to the present invention is characterized in that the variable spectrum element includes: a pair of optical substrates which are arranged opposite at a distance from each other; first, second, third, and fourth capacitive sensors each of which includes a pair of electrodes that are placed on the surfaces of the pair of the optical substrates opposite to each other respectively and each of which detects a distance between the surfaces of the pair of the optical substrates opposite to each other at each placed position; and first, second, third, and fourth actuators which relatively move one of the pair of the optical substrates relative to the other optical substrate to change a distance between the surfaces of the pair of the optical substrates opposite to each other, wherein: the first and third capacitive sensors are placed at positions at which the first and third capacitive sensors are symmetrical with respect to a line connecting the centers of mass of the surfaces of the pair of the optical substrates opposite to each other, respectively; the second and fourth capacitive sensors are placed at positions at which the second and fourth capacitive sensors are symmetrical with respect to the line connecting the centers of mass of the surfaces of the pair of the optical substrates opposite to each other, respectively; the first, second, third, and fourth actuators are placed on lines running from the center of mass of the surface of each of the pair of the optical substrates opposite to each other to the centers of the first, second, third, and fourth capacitive sensors respectively, respectively; and the variable spectrum element includes a control unit, the control unit calculating a distance between the centers of mass of the surfaces of the pair of the optical substrates opposite to each other with signals from the first, second, third, and fourth capacitive sensors, the control unit calculating, with signals from the first and third capacitive sensors, a first angle that is made between the surface perpendicular to the line connecting the centers of mass of the surfaces of the pair of the optical substrates and the surface of the relatively moved optical substrate of the surfaces of the pair of the optical substrates opposite to each other, the control unit calculating, with signals from the second and fourth capacitive sensors, a second angle that is made between the surface perpendicular to the line connecting the centers of mass of the surfaces of the pair of the optical substrates and the surface of the relatively moved optical substrate of the surfaces of the pair of the optical substrates opposite to each other, the control unit calculating with signals from the first and second capacitive sensors a difference between: a distance between the surfaces of the pair of the optical substrates opposite to each other at a position of the first actuator placed on the pair of the optical substrates; and a distance between the surfaces of the pair of the optical substrates opposite to each other at a position of the second actuator placed on the pair of the optical substrate, the control unit actuating the first and third actuators on the basis of the distance between the centers of mass of the surfaces of the optical substrates, the first angle, and the difference between the distance between the surfaces of the pair of the optical substrates opposite to each other at the placed position of the first actuator and the distance between the surfaces of the pair of the optical substrates opposite to each other at the placed position of the second actuator, the control unit actuating the second and fourth actuators on the basis of the distance between the centers of mass of the surfaces of the optical substrates, the second angle, and the difference between the distance between the surfaces of the pair of the optical substrates opposite to each other at the placed position of the first actuator and the distance between the surfaces of the pair of the optical substrates opposite to each other at the placed position of the second actuator, and the control unit repeating the process which ranges from the calculation of a distance between the centers of mass of the surfaces of the optical substrates to the actuations of the second and fourth actuators until the difference between the distance between the surfaces of the pair of the optical substrates opposite to each other at the placed position of the first actuator and the distance between the surfaces of the pair of the optical substrates opposite to each other at the placed position of the second actuator becomes approximately equal to zero.

Also, in a variable spectrum element according to the present invention, it is preferred that: the first, second, third, and fourth capacitive sensors and the first, second, third, and fourth actuators are placed at positions at which the first, second, third, and fourth capacitive sensors overlap with the first, second, third, and fourth actuators respectively when these capacitive sensors and these actuators are viewed from a direction along the line connecting the centers of mass of the surfaces of the pair of the optical substrates opposite to each other, respectively; and the following conditions are satisfied:

$$x_1 = x - r \sin \theta$$

$$x_2 = x - r \sin \phi$$

$$x_3 = x + r \sin \theta$$

$$x_4 = x + r \sin \phi$$

where x denotes a distance between the centers of mass of the surfaces of the pair of the optical substrates, $x_1$, $x_2$, $x_3$, and $x_4$ denote distances between the surfaces of the pair of the optical substrates opposite to each other at the positions at which the first, second, third, and fourth capacitive sensors are placed respectively, respectively, $\theta$ denotes the first angle, $\phi$ denotes the second angle, and r denotes a distance between the center of mass of the surface of the relatively moved optical substrate of the surfaces of the pair of the optical substrates opposite to each other and the position of each of the first to fourth capacitive sensors placed on the surface of the relatively moved optical substrate.

Also, in a variable spectrum element according to the present invention, it is preferred that: the control unit calculates a distance between the centers of mass of the surfaces of the optical substrates with the average of distances between the surfaces of the pair of the optical substrates opposite to each other at the positions at which the first, second, third, and fourth capacitive sensors are placed respectively; the control unit calculates the first angle with a difference between distances between the surfaces of the pair of the optical substrates opposite to each other at the positions at which the first and third capacitive sensors are placed respectively; the control unit calculates the second angle with a difference between distances between the surfaces of the pair of the optical substrates opposite to each other at the positions at which the second and fourth capacitive sensors are placed respectively; and the control unit calculates a difference between the distance between the surfaces of the pair of the optical substrates opposite to each other at the placed position of the first actuator and the distance between the surfaces of the pair of the optical substrates opposite to each other at the placed position of the second actuator, with a difference between a distance between the surfaces of the pair of the optical substrates opposite to each other at the position of the first capacitive sensor placed and a distance between the surfaces of the pair of the optical substrates opposite to each other at the position of the second capacitive sensor placed.

Also, in a variable spectrum element according to the present invention, it is preferred that: the first, second, third, and fourth capacitive sensors and the first, second, third, and fourth actuators are placed at positions at which the first, second, third, and fourth capacitive sensors overlap with the first, second, third, and fourth actuators respectively when these capacitive sensors and these actuators are viewed from a direction along the line connecting the centers of mass of the surfaces of the pair of the optical substrates opposite to each other, respectively; and the following conditions are satisfied:

$$x = (x_1 + x_2 + x_3 + x_4)/4$$

$$\theta = R_1(x_3 - x_1)$$

$$\phi = R_2(x_4 - x_2)$$

where x denotes a distance between the centers of mass of the surfaces of pair of the optical substrates, $x_1$, $x_2$, $x_3$, and $x_4$ denote distances between the surfaces of the pair of the optical substrates opposite to each other at the positions at which the first, second, third, and fourth capacitive sensors are placed respectively, respectively, $\theta$ denotes the first angle, $\phi$ denotes the second angle, and $R_1$ and $R_2$ denote predetermined coefficients.

Also, a variable spectrum element according to the present invention is characterized in that the variable spectrum element includes: a pair of optical substrates which are arranged opposite at a distance from each other; first, second, third, and fourth capacitive sensors each of which includes a pair of electrodes that are placed on the surfaces of the pair of the optical substrates opposite to each other respectively and each of which detects a distance between the surfaces of the pair of the optical substrates opposite to each other at each placed position; and first, second, third, and fourth actuators which relatively move one of the pair of the optical substrates relative to the other optical substrate to change a distance between the surfaces of the pair of the optical substrates opposite to each other, wherein: the first and third capacitive sensors are placed at positions at which the first and third capacitive sensors are symmetrical with respect to a line connecting the centers of mass of the surfaces of the pair of the optical substrates opposite to each other, respectively; the second and fourth capacitive sensors are placed at positions at which the second and fourth capacitive sensors are symmetrical with respect to the line connecting the centers of mass of the surfaces of the pair of the optical substrates opposite to each other, respectively; the first, second, third, and fourth capacitive sensors and the first, second, third, and fourth actuators are placed on a circle at regular intervals one after the other when these capacitive sensors and these actuators are viewed from a direction along the line connecting the centers of mass of the surfaces of the pair of the optical substrates opposite to each other; and the variable spectrum element includes a control unit, the control unit calculating a distance between the centers of mass of the surfaces of the pair of the optical substrates opposite to each other with signals from the first, second, third, and fourth capacitive sensors, the control unit calculating with signals from the first, second, third, and fourth capacitive sensors distances between the surfaces of the pair of the optical substrates opposite to each other at positions of the first, second, third, and fourth actuators placed on the pair of the optical substrates respectively, the control unit calculating, with the values of the distances between the surfaces of the pair of the optical substrates opposite to each other at the placed positions of the first and third actuators, a first angle that is made between the surface perpendicular to the line connecting the centers of mass of the surfaces of the pair of the optical substrates and the surface of the relatively moved optical substrate of the surfaces of the pair of the optical substrates opposite to each other, the control unit calculating, with the values of the distances between the surfaces of the pair of the optical substrates opposite to each other at the placed positions of the second and fourth actuators, a second angle that is made between the surface perpendicular to the line connecting the centers of mass of the surfaces of the pair of the optical substrates and the surface of the relatively moved optical substrate of the surfaces of the pair of the optical substrates opposite to each other, the control unit actuating the first and third actuators on the basis of the distance between the centers of mass of the surfaces of the optical substrates, the first angle, and a difference between: the distance between the surfaces of the pair of the optical substrates opposite to each other at the placed position of the first actuator; and the distance between the surfaces of the pair of the optical substrates opposite to each other at the placed position of the second actuator, the control unit actuating the second and fourth actuators on the basis of the distance between the centers of mass of the surfaces of the optical substrates, the second angle, and the difference between the distance between the surfaces of the pair of the optical substrates opposite to each other at the placed position of the first actuator and the distance between the surfaces of the pair of the optical substrates opposite to each other at the placed position of the second actuator, and the control unit repeating the process which ranges from the calculation of a distance between the centers of mass of the surfaces of the optical substrates to the actuations of the second and fourth actuators until the difference between the distance between the surfaces of the pair of the optical substrates opposite to each other at the placed position of the first actuator and the distance between the surfaces of the pair of the optical substrates opposite to each other at the placed position of the second actuator becomes approximately equal to zero.

Also, a variable spectrum element according to the present invention is characterized in that the variable spectrum element includes: a pair of optical substrates which are arranged opposite at a distance from each other; first, second, third, and fourth capacitive sensors each of which includes a pair of electrodes that are placed on the surfaces of the pair of the optical substrates opposite to each other respectively and each of which detects a distance between the surfaces of the pair of the optical substrates opposite to each other at each placed position; and first, second, third, and fourth actuators which relatively move one of the pair of the optical substrates relative to the other optical substrate to change a distance between the surfaces of the pair of the optical substrates opposite to each other, wherein: the first and third capacitive sensors are placed at positions at which the first and third capacitive sensors are symmetrical with respect to a line connecting the centers of mass of the surfaces of the pair of the optical substrates opposite to each other, respectively; the second and fourth capacitive sensors are placed at positions at which the second and fourth capacitive sensors are symmetrical with respect to the line connecting the centers of mass of the surfaces of the pair of the optical substrates opposite to each other, respectively; the first, second, third, and fourth actuators are placed on lines running from the center of mass of the surface of each of the pair of the optical substrates opposite to each other to the centers of the first, second, third, and fourth capacitive sensors respectively, respectively; and the variable spectrum element includes a control unit, the control unit calculating a distance between the centers of mass of the surfaces of the pair of the optical substrates opposite to each other with signals from the first, second, third, and fourth capacitive sensors, the control unit calculating, with signals from the first and third capacitive sensors, a first angle that is made between the surface perpendicular to the line connecting the centers of mass of the surfaces of the pair of the optical substrates and the surface of the relatively moved optical substrate of the surfaces of the pair of the optical substrates opposite to each other, the control unit calculating, with signals from the second and fourth capacitive sensors, a second angle that is made between the surface perpendicular to the line connecting the centers of mass of the surfaces of the pair of the optical substrates and the surface of the relatively moved optical substrate of the surfaces of the pair of the optical substrates opposite to each other, the control unit calculating with signals from the first and third capacitive sensors the average of the first directional surface distances that is obtained by taking the average of: a distance between the surfaces of the pair of the optical substrates opposite to each other at a position of the first actuator placed on the pairs of the optical substrates; and a distance between the surfaces of the pair of the optical substrates opposite to each other at a position of the third actuator placed on the pairs of the optical substrates, the control unit calculating with signals from the second and fourth capacitive sensors the average of the second directional surface distances that is obtained by taking the average of: a distance between the surfaces of the pair of the optical substrates opposite to each other at a position of the second actuator placed on the pair of the optical substrates; and a distance between the surfaces of the pair of the optical substrates opposite to each other at a position of the fourth actuator placed on the pair of the optical substrates, the control unit calculating a difference between the average of the first directional surface distances and the average of the second directional surface distances, the control unit actuating the first and third actuators on the basis of the distance between the centers of mass of the surfaces of the optical substrates, the first angle, and the difference between the average of the first directional surface distances and the average of the second directional surface distances, the control unit actuating the second and fourth actuators on the basis of the distance between the centers of mass of the surfaces of the optical substrates, the second angle, and the difference between the average of the first directional surface distances and the average of the second directional surface distances, and the control unit repeating the process which ranges from the calculation of a distance between the centers of mass of the surfaces of the optical substrates to the actuations of the second and fourth actuators until the difference between the average of the first directional surface distances and the average of the second directional surface distances becomes approximately equal to zero.

Also, in a variable spectrum element according to the present invention, it is preferred that: the first, second, third, and fourth capacitive sensors and the first, second, third, and fourth actuators are placed at positions at which the first, second, third, and fourth capacitive sensors overlap with the first, second, third, and fourth actuators respectively when these capacitive sensors and these actuators are viewed from a direction along the line connecting the centers of mass of the surfaces of the pair of the optical substrates opposite to each other, respectively; and the following conditions are satisfied:

$$x_1 = x - r \sin \theta$$

$$x_2 = x - r \sin \phi$$

$$x_3 = x + r \sin \theta$$

$$x_4 = x + r \sin \phi$$

where x denotes a distance between the centers of mass of the surfaces of the pair of the optical substrates, $x_1$, $x_2$, $x_3$, and $x_4$ denote distances between the surfaces of the pair of the optical substrates opposite to each other at the positions at which the first, second, third, and fourth capacitive sensors are placed respectively, respectively, $\theta$ denotes the first angle, $\phi$ denotes the second angle, and r denotes a distance between the center of mass of the surface of the relatively moved optical substrate of the surfaces of the pair of the optical substrates opposite to each other and the position of each of the first to fourth capacitive sensors placed on the surface of the relatively moved optical substrate.

Also, in a variable spectrum element according to the present invention, it is preferred that: the control unit calculates a distance between the centers of mass of the surfaces of the optical substrates with the average of distances between the surfaces of the pair of the optical substrates opposite to each other at the positions at which the first, second, third, and fourth capacitive sensors are placed respectively; the control unit calculates the first angle with a difference between distances between the surfaces of the pair of the optical substrates opposite to each other at the positions at which the first and third capacitive sensors are placed respectively; the control unit calculates the second angle with a difference between distances between the surfaces of the pair of the optical substrates opposite to each other at the positions at which the second and fourth capacitive sensors are placed respectively; and the control unit calculates a difference between the average of the first directional surface distances and the average of the second directional surface distances, by calculating a difference between: the average of the distance between the surfaces of the pair of the optical substrates opposite to each other at the position of the first capacitive sensor placed and the distance between the surfaces of the pair of the optical substrates opposite to each other at the position of the third capacitive sensor placed; and the average of the distance between the surfaces of the pair of the optical substrates opposite to each other at the position of the second capacitive sensor placed and the distance between the surfaces of the pair of the optical substrates opposite to each other at the position of the fourth capacitive sensor placed.

Also, in a variable spectrum element according to the present invention, it is preferred that: the first, second, third, and fourth capacitive sensors and the first, second, third, and fourth actuators are placed at positions at which the first, second, third, and fourth capacitive sensors overlap with the first, second, third, and fourth actuators respectively when these capacitive sensors and these actuators are viewed from a direction along the line connecting the centers of mass of the surfaces of the pair of the optical substrates opposite to each other, respectively; and the following conditions are satisfied:

$$x=(x_1+x_2+x_3+x_4)/4$$

$$\theta=R_1(x_3-x_1)$$

$$\phi=R_2(x_4-x_2)$$

where x denotes a distance between the centers of mass of the surfaces of pair of the optical substrates, $x_1$, $x_2$, $x_3$, and $x_4$ denote distances between the surfaces of the pair of the optical substrates opposite to each other at the positions at which the first, second, third, and fourth capacitive sensors are placed respectively, respectively, $\theta$ denotes the first angle, $\phi$ denotes the second angle, and $R_1$ and $R_2$ denote predetermined coefficients.

Also, a variable spectrum element according to the present invention is characterized in that: the variable spectrum element includes: a pair of optical substrates which are arranged opposite at a distance from each other; first, second, third, and fourth capacitive sensors each of which includes a pair of electrodes that are placed on the surfaces of the pair of the optical substrates opposite to each other respectively and each of which detects a distance between the surfaces of the pair of the optical substrates opposite to each other at each placed position; and first, second, third, and fourth actuators which relatively move one of the pair of the optical substrates relative to the other optical substrate to change a distance between the surfaces of the pair of the optical substrates opposite to each other, wherein: the first and third capacitive sensors are placed at positions at which the first and third capacitive sensors are symmetrical with respect to a line connecting the centers of mass of the surfaces of the pair of the optical substrates opposite to each other, respectively; the second and fourth capacitive sensors are placed at positions at which the second and fourth capacitive sensors are symmetrical with respect to the line connecting the centers of mass of the surfaces of the pair of the optical substrates opposite to each other, respectively; the first, second, third, and fourth capacitive sensors and the first, second, third, and fourth actuators are placed on a circle at regular intervals one after the other when these capacitive sensors and these actuators are viewed from a direction along the line connecting the centers of mass of the surfaces of the pair of the optical substrates opposite to each other; and the variable spectrum element includes a control unit, the control unit calculating a distance between the centers of mass of the surfaces of the pair of the optical substrates opposite to each other with signals from the first, second, third, and fourth capacitive sensors, the control unit calculating, with signals from the first, second, third, and fourth capacitive sensors, distances between the surfaces of the pair of the optical substrates opposite to each other at positions of the first, second, third, and fourth actuators placed on the pair of the optical substrates respectively, the control unit calculating the average of the first directional surface distances that is obtained by taking the average of the distances between the surfaces of the pair of the optical substrates opposite to each other at the positions of the first and third actuators placed on the pair of the optical substrates respectively and the control unit calculating the average of the second directional surface distances that is obtained by taking the average of the distances between the surfaces of the pair of the optical substrates opposite to each other at the positions of the second and fourth actuators placed on the pair of the optical substrates respectively, the control unit calculating, with the values of the distances between the surfaces of the pair of the optical substrates opposite to each other at the placed positions of the first and third actuators, a first angle that is made between the surface perpendicular to the line connecting the centers of mass of the surfaces of the pair of the optical substrates and the surface of the relatively moved optical substrate of the surfaces of the pair of the optical substrates opposite to each other, the control unit calculating, with the values of the distances between the surfaces of the pair of the optical substrates opposite to each other at the placed positions of the second and fourth actuators, a second angle that is made between the surface perpendicular to the line connecting the centers of mass of the surfaces of the pair of the optical substrates and the surface of the relatively moved optical substrate of the surfaces of the pair of the optical substrates opposite to each other, the control unit actuating the first and third actuators on the basis of the distance between the centers of mass of the surfaces of the optical substrates, the first angle, and a difference between the average of the first directional surface distances and the average of the second directional surface distances, the control unit actuating the second and fourth actuators on the basis of the distance between the centers of mass of the surfaces of the optical substrates, the second angle, and the difference between the average of the first directional surface distances and the average of the second directional surface distances, and the control unit repeating the process which ranges from the calculation of a distance between the centers of mass of the surfaces of the optical substrates to the actuations of the second and fourth actuators until the difference between the average of the first directional surface distances and the average of the second directional surface distances becomes approximately equal to zero.

Also, it is preferred that one of the above-described variable spectrum elements according to the present invention includes a property difference correction voltage applying unit by which an offset voltage for cancelling a difference between the properties of the first, second, third, and fourth actuators is applied to each of the first, second, third, and fourth actuators in operating the control unit.

These and other features and advantages of the present invention will become apparent from the following detailed description of the preferred embodiments when taken in conjunction with the accompanying drawings.

BRIEF DESCRIPTION OF THE DRAWINGS

FIG. 6A is a graph showing the response characteristic in the case where a surface distance is controlled in a variable spectrum element in the prior art, and FIG. 6B is a graph showing the response characteristic in the case where a surface distance is controlled in the variable spectrum element according to the present embodiment.

DETAILED DESCRIPTION OF THE PREFERRED EMBODIMENTS

The embodiments of the present invention will be explained in detail below, using the drawings.

Embodiment 1

Figure 1:
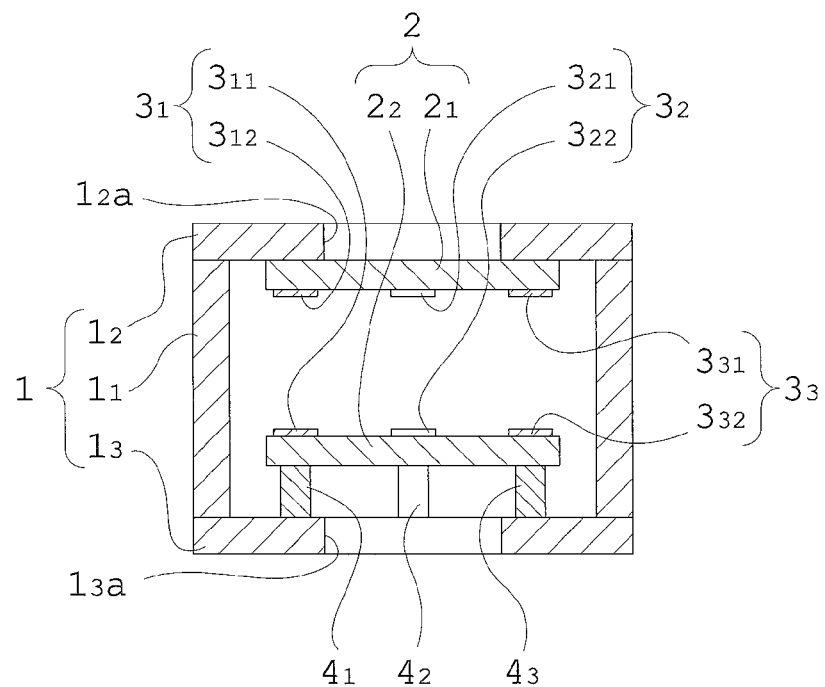
FIG. 1 is a cross sectional view showing an etalon device in a variable spectrum element according to an embodiment 1.
Figure 2:
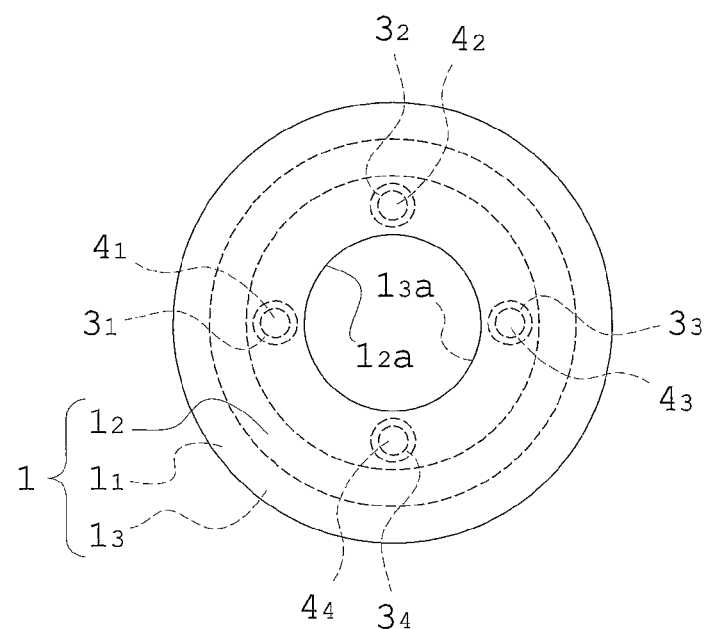
FIG. 2 is a plane view showing the etalon device shown in FIG. 1.
Figure 3:
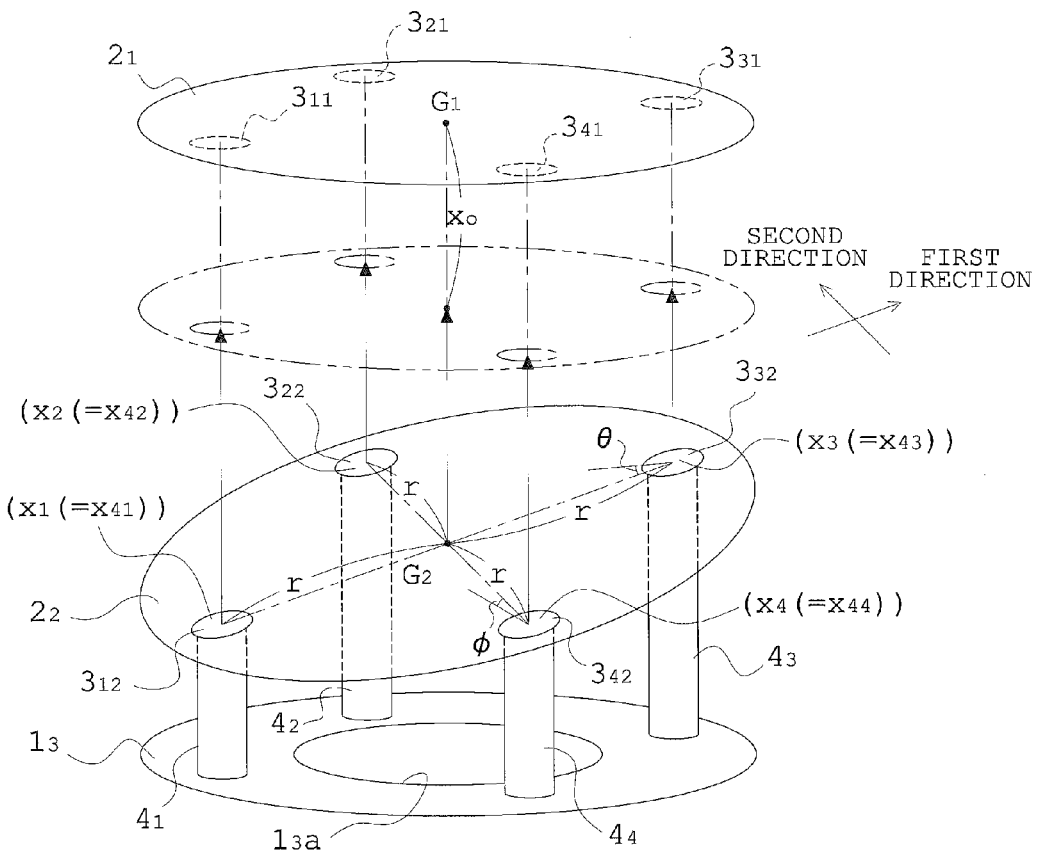
FIG. 3 is a schematic view showing actuations of a pair of optical substrates and four piezoelectric devices which are provided for the etalon device shown in FIG. 1.
Figure 4:
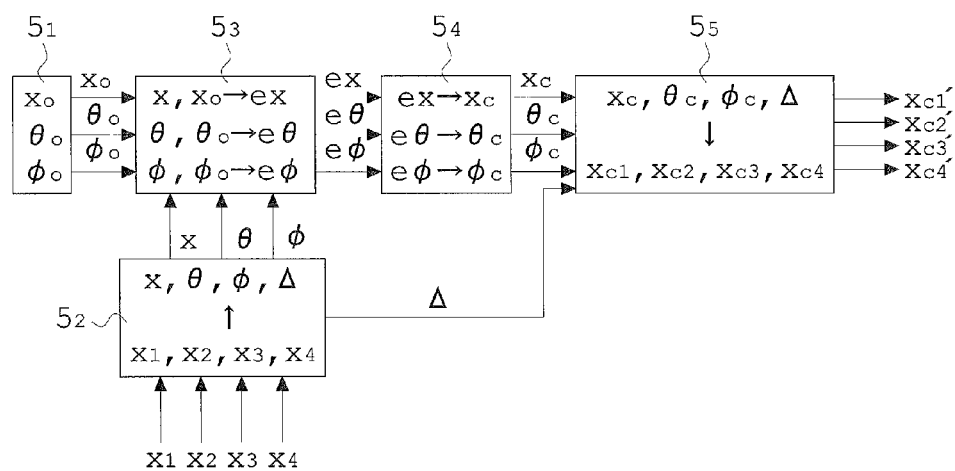
FIG. 4 is a block diagram showing an operation which is performed by a control unit of the variable spectrum element according to the embodiment 1.
Figure 5:
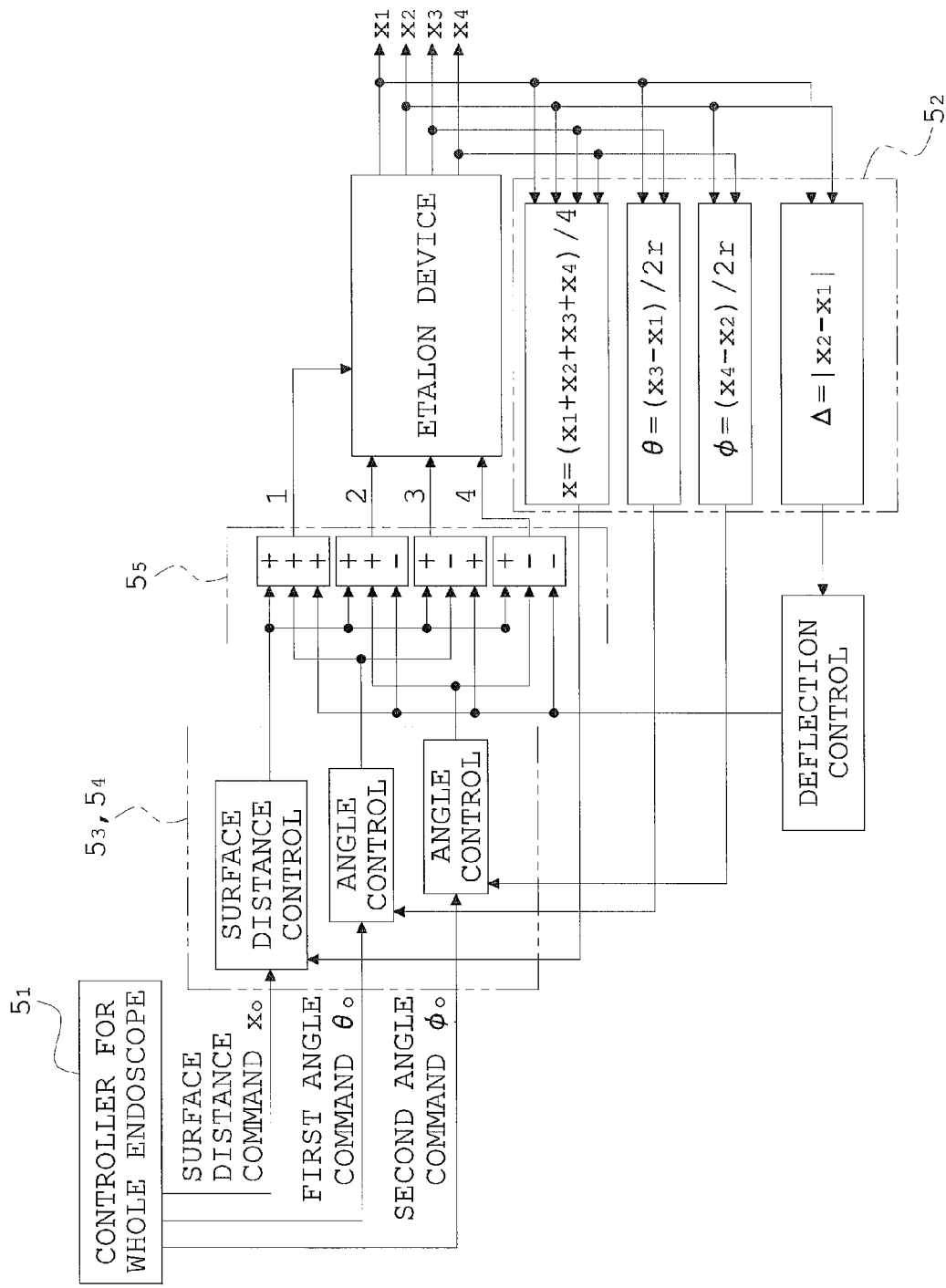
FIG. 5 is a block diagram schematically showing the whole of a structure of control in the variable spectrum element according to the embodiment 1.
Figure 6A:
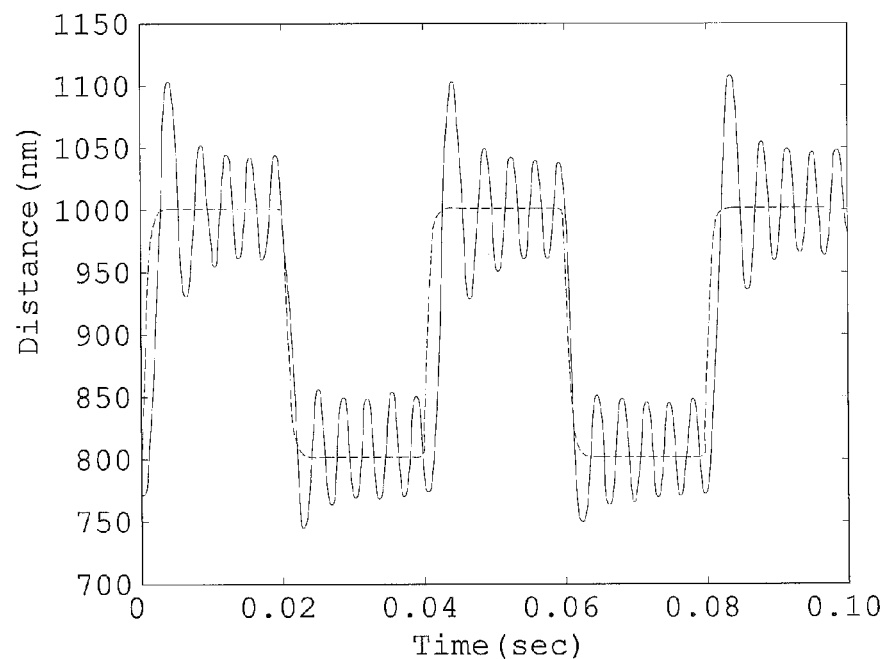
FIGS. 6A and 6B are graphs showing the response characteristic of the etalon device shown in FIG. 1. To be specific.
Figure 6B:
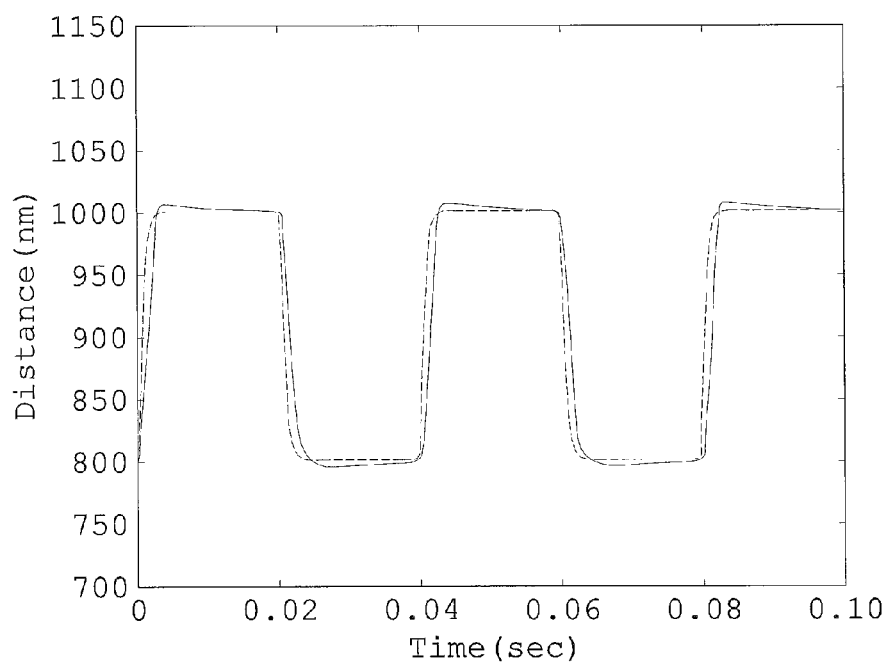

FIG. 1 is a cross sectional view showing an etalon device in a variable spectrum element according to the present embodiment. FIG. 2 is a plane view showing the etalon device shown in FIG. 1. FIG. 3 is a schematic view showing actuations of a pair of optical substrates and four piezoelectric devices in the etalon device shown in FIG. 1. FIG. 4 is a block diagram showing an operation which is performed by a control unit of the variable spectrum element according to the embodiment 1. FIG. 5 is a block diagram schematically showing the whole of a structure of control in the variable spectrum element according to the embodiment 1. FIGS. 6A and 6B are graphs showing the response characteristic of the etalon device shown in FIG. 1. To be specific, FIG. 6A is a graph showing the response characteristic in the case where a surface distance is controlled in a variable spectrum element in the prior art, and FIG. 6B is a graph showing the response characteristic in the case where a surface distance is controlled in the variable spectrum element according to the present embodiment.

The variable spectrum element according to the present embodiment includes an etalon device which is shown in FIGS. 1 and 2 and a control unit which is not shown in the drawings.

First, the constitution of the etalon device for this variable spectrum element is explained using FIGS. 1 and 2.

As shown in FIGS. 1 and 2, this etalon device includes a pair of optical substrates 2, capacitive sensors which are a means of measuring a distance between the surfaces of the pair of the optical substrates 2 opposite to each other, and piezoelectric devices which are actuators for moving one substrate of the pair of the optical substrates 2 and the actuation of which is controlled by the control unit not shown in the drawings, the pair of the optical substrates 2, the capacitive sensors, and the piezoelectric devices being placed on the inside of an outer frame 1 of the etalon device.

The outer frame 1 is formed by fitting an annular member $1_2$ to one end surface of a cylindrical member $1_1$ and fitting an annular member $1_3$ to the other end surface of the cylindrical member $1_1$.

Also, circular openings $1_2a$ and $1_3a$ are formed in the approximately middle portions of the annular members $1_2$ and $1_3$, respectively. And, light passes through the openings $1_2a$ and $1_3a$ in this etalon device.

The pair of the optical substrates 2 consists of a fixed substrate $2_1$ and a movable substrate $2_2$ which are arranged while the surfaces of these substrates opposite to each other are being separated by a distance in space and are being parallel to each other. In the optical substrates 2, the fixed substrate $2_1$ is a disk-like optical member which is fixed to the annular member $1_2$ of the outer frame 1 on the inside of the outer frame 1 while crossing the axis of light passing through the openings $1_2a$ and $1_3a$. On the other hand, the movable substrate $2_2$ is a disk-like optical member which is held by the piezoelectric devices while crossing light passing through the openings $1_2a$ and $1_3a$.

Such a pair of the optical substrates 2 is formed to operate in such a way that the piezoelectric devices move the movable substrate $2_2$ along the axis of light passing through the openings $1_2a$ and $1_3a$, or along the line connecting the centers of mass of the surfaces of the pair of the optical substrates opposite to each other, so that a distance between the surfaces of the optical substrates opposite to each other can be changed.

A first capacitive sensor $3_1$, a second capacitive sensor $3_2$, a third capacitive sensor $3_3$, and a fourth capacitive sensor $3_4$ consist of a pair of electrodes $3_{11}$ and $3_{12}$, a pair of electrodes $3_{21}$ and $3_{22}$, a pair of electrodes $3_{31}$ and $3_{32}$, and a pair of electrodes $3_{41}$ and $3_{42}$, respectively. And, these pairs of the electrodes are arranged respectively at positions on the surfaces of the pair of the optical substrates 2 at which these electrodes do not intercept light passing through the openings $1_2a$ and $1_3a$ of the outer frame 1 while the electrodes of each of the pairs of the electrodes are facing each other, the surfaces of the pair of the optical substrates 2 being opposite to each other Besides, the characteristics of these capacitive sensors are that the capacitance between the electrodes of each capacitive sensor changes in inverse proportion to a distance between the surfaces of the optical substrates. And, in this etalon device, values acquired by these capacitive sensors are transformed into values of distances between the surfaces of the optical substrates 2 to be outputted to the control unit which is not shown in the drawings.

A first piezoelectric device $4_1$, a second piezoelectric device $4_2$, a third piezoelectric device $4_3$, and a fourth piezoelectric device $4_4$ are fixed to the annular member $1_3$ of the outer frame 1 on the inside of the outer frame 1 with these piezoelectric devices not intercepting light that passes through the openings $1_2a$ and $1_3a$.

And, the first, second, third, and fourth capacitive sensors $3_1$, $3_2$, $3_3$, and $3_4$ and the first, second, third, and fourth piezoelectric devices $4_1$, $4_2$, $4_3$, and $4_4$ are arranged at positions at which the first piezoelectric device $4_1$ overlaps with the first capacitive sensor $3_1$, the second piezoelectric device $4_2$ overlaps with the second capacitive sensor $3_2$, the third piezoelectric device $4_3$ overlaps with the third capacitive sensor $3_3$, and the fourth piezoelectric device $4_4$ overlaps with the fourth capacitive sensor $3_4$, respectively, when these capacitive sensors and these piezoelectric devices are viewed from the direction along the line connecting the centers of mass of the surfaces of the pair of the optical substrates 2 opposite to each other.

Also, the first capacitive sensor $3_1$, the third capacitive sensor $3_3$, the first piezoelectric device $4_1$, and the third piezoelectric device $4_3$ are arranged at positions at which the first capacitive sensor $3_1$ and the first piezoelectric device $4_1$ are symmetrical to the third capacitive sensor $3_3$ and the third piezoelectric device $4_3$ with respect to the line connecting the centers of mass of the surfaces of the pair of the optical substrates 2 opposite to each other, respectively, when the first and third capacitive sensors and the first and third piezoelectric devices are viewed from the direction along the line connecting the centers of mass of the surfaces of the pair of the optical substrates 2.

On the other hand, the second capacitive sensor $3_2$, the fourth capacitive sensor $3_4$, the second piezoelectric device $4_2$, and the fourth piezoelectric device $4_4$ are arranged at positions at which the second capacitive sensor $3_2$ and the second piezoelectric device $4_2$ are symmetrical to the fourth capacitive sensor $3_4$ and the fourth piezoelectric device $4_4$ with respect to the line connecting the centers of mass of the surfaces of the pair of the optical substrates 2 opposite to each other, respectively, when the second and fourth capacitive sensors and the second and fourth piezoelectric devices are viewed from the direction along the line connecting the centers of mass of the surfaces of the pair of the optical substrates 2.

In this embodiment, the first capacitive sensor $3_1$ and the first piezoelectric device $4_1$, the second capacitive sensor $3_2$ and the second piezoelectric device $4_2$, the third capacitive sensor $3_3$ and the third piezoelectric device $4_3$, and the fourth capacitive sensor $3_4$ and the fourth piezoelectric device $4_4$ are arranged at regular intervals when these capacitive sensors and these piezoelectric devices are viewed from the direction along the line connecting the centers of mass of the surfaces of the pair of the optical substrates 2 opposite to each other.

Next, actuation of and control of the movable substrate $2_2$ in the etalon device for the variable spectrum element according to the present embodiment are explained using FIG. 3.

As shown in FIG. 3, when the movable substrate $2_2$ is moved relative to the fixed substrate $2_1$ so that a surface distance between the pair of the optical substrates 2 has a value of $x_0$, etalon devices in the prior art are operated in such a way that: the first piezoelectric device $4_1$ is actuated on the basis of an output value of the first capacitive sensor $3_1$ so that the surface distance at the position at which the first capacitive sensor $3_1$ is placed has the target value of $x_0$; and, similarly, the second piezoelectric device $4_2$ is actuated on the basis of an output value of the second capacitive sensor $3_2$, the third piezoelectric device $4_3$ is actuated on the basis of an output value of the third capacitive sensor $3_3$, and the fourth piezoelectric device $4_4$ is actuated on the basis of an output value of the fourth capacitive sensor $3_4$, in order to make a surface distance between the pair of the optical substrates 2 have the target value of $x_0$.

However, in such control, for example, even though the first piezoelectric device $4_1$ is accurately actuated and a distance between the surfaces of the pair of the optical substrates 2 at the position at which the first capacitive sensor $3_1$ is placed is made to have the target value of $x_0$, interference causing in actuating the second and fourth piezoelectric devices $4_2$ and $4_4$ that are placed to be adjacent to the first piezoelectric device $4_1$ afterward may inevitably make the surface distance at the position change from the target value of $x_0$.

There is a way of using feedback control such as PID control (Proportional Integral Derivative Control) as a way of solving the above problem. However, in this case, it takes a long time to make the surface distance between the optical substrates reach the target value of $x_0$.

Also, another ways of solving the above problem include a way of giving each of the piezoelectric devices a value which is calculated in advance against the interference from another piezoelectric device as a command value. However, a calculation of that command value is very complicated, so that it takes a long time to make the surface distance between the pair of the optical substrates 2 reach the target value of $x_0$, similarly.

Accordingly, in the variable spectrum element according to the present embodiment, four output values from the first to fourth capacitive sensors $3_1$, $3_2$, $3_3$, and $3_4$ are transformed into three parameters and the operations are performed so that actuation control of the first to fourth piezoelectric devices $4_1$, $4_2$, $4_3$, and $4_4$ is performed.

Now, operations which are carried out by the control unit for the variable spectrum element according to the present embodiment are explained in detail using FIGS. 3 to 6.

When the movable substrate $2_2$ is moved relative to the fixed substrate $2_1$ so that a surface distance between the pair of the optical substrates 2 has a value of $x_0$ as shown in FIG. 3 in the variable spectroscopic member according to the present embodiment, the target value $x_0$ of a distance between the center of mass $G_1$ of the surface of the fixed substrate $2_1$ and the center of mass $G_2$ of the surface of the movable substrate $2_2$, these surfaces being opposite to each other, a target value $\theta_0$ of the first angle made between the surface perpendicular to the line connecting the centers of mass $G_1$ and $G_2$ and the surface of the movable substrate $2_2$ opposite to the surface perpendicular to the line, and a target value $\phi_0$ of the second angle made between the surface perpendicular to the line connecting the centers of mass $G_1$ and $G_2$ and the surface of the movable substrate $2_2$ opposite to the surface perpendicular to the line are first inputted into the control unit through a target value input unit $5_1$, as shown in FIGS. 3 and 4.

Next, a sensor output transformation unit $5_2$ acquires surface distances $x_1$, $x_2$, $x_3$, and $x_4$ between the pair of the optical substrates 2 at the positions at which the first, second, third, and fourth capacitive sensors $3_1$, $3_2$, $3_3$, and $3_4$ are placed respectively, the surface distances $x_1$, $x_2$, $x_3$, and $x_4$ at the respective positions being measured by these capacitive sensors $3_1$, $3_2$, $3_3$, and $3_4$ respectively. And then, the sensor output transformation unit $5_2$ not only calculates a difference value $\Delta(=|x_2-x_1|)$ between the surface distances $x_1$ and $x_2$ between the optical substrates but also transforms the surface distances $x_1$, $x_2$, $x_3$, and $x_4$ into the current value x of a distance between the centers of mass $G_1$ and $G_2$, the current value $\theta$ of the first angle, and the current value $\phi$ of the second angle.

Besides, in the present embodiment, the first, second, third, and fourth capacitive sensors $3_1$, $3_2$, $3_3$, and $3_4$ and the first, second, third, and fourth piezoelectric devices $4_1$, $4_2$, $4_3$, and $4_4$ are placed at the positions at which the first, second, third, and fourth piezoelectric devices $4_1$, $4_2$, $4_3$, and $4_4$ overlap with the first, second, third, and fourth capacitive sensors $3_1$, $3_2$, $3_3$, and $3_4$ respectively, respectively, when these capacitive sensors $3_1$, $3_2$, $3_3$, and $3_4$ and these piezoelectric devices $4_1$, $4_2$, $4_3$, and $4_4$ are viewed from the direction along the line connecting the centers of mass of the surfaces of the pair of the optical substrates 2 opposite to each other. As a result, distances $x_{41}$, $x_{42}$, $x_{43}$, and $x_{44}$ between the surfaces of the pair of the optical substrates 2 opposite to each other at the positions of the first, second, third, and fourth piezoelectric devices $4_1$, $4_2$, $4_3$, and $4_4$ placed respectively correspond with distances $x_1$, $x_2$, $x_3$, and $x_4$ between the surfaces of the pair of the optical substrates 2 opposite to each other at the positions of the first, second, third, and fourth capacitive sensors $3_1$, $3_2$, $3_3$, and $3_4$ placed respectively.

Specifically, the distance x between the centers of mass of the surfaces of the pair of the optical substrates 2 opposite to each other is found by the following formula:

$$x=(x_1+x_2+x_3+x_4)/4.$$

Also, the first and second angles $\theta$ and $\phi$ which are made between the surface perpendicular to the line connecting the centers of mass of the surfaces of the pair of the optical substrates 2 and the surface of the movable substrate $2_2$ opposite to the fixed substrate $2_1$ are expressed by the following formulas with known distances $r_{31}$, $r_{32}$, $r_{33}$, and $r_{34}$ from the center of mass $G_2$ of the surface of the movable substrate $2_2$ to the centers of the electrodes $3_{12}$, $3_{22}$, $3_{32}$, and $3_{42}$ of the first to fourth capacitive sensors $3_1$, $3_2$, $3_3$, and $3_4$ respectively on the surface of the movable substrate $2_2$:

$$\sin\theta=(x_3-x_1)/(r_{31}+r_{33})$$

$$\sin\phi=(x_4-x_2)/(r_{32}+r_{34}).$$

Besides, in the present embodiment, $$r_{31}=r_{32}=r_{33}=r_{34}=r,$$

and, both of the first angle $\theta$ and the second angle $\phi$ are sufficiently small, so that the first angle $\theta$ and the second angle $\phi$ are found by the following formulas:

$$\theta=(x_3-x_1)/2r$$

$$\phi=(x_4-x_2)/2r.$$

Next, a difference value calculating unit $5_3$ calculates a value ex of a difference between the target value $x_0$ inputted through the target value input unit $5_1$ and the value x transformed by the sensor output transformation unit $5_2$, a value $e\theta$ of a difference between the target value $\theta_0$ inputted through the target value input unit $5_1$ and the value $\theta$ transformed by the sensor output transformation unit $5_2$, and a value $e\phi$ of a difference between the target value $\phi_0$ inputted through the target value input unit $5_1$ and the value $\phi$ transformed by the sensor output transformation unit $5_2$.

Next, a command value calculating unit $5_4$ carries out PID control on the basis of the difference values ex, $e\theta$, and $e\phi$ that are calculated by the difference value calculating unit $5_3$, and the command value calculating unit $5_4$ finds command values $x_c$, $\theta_c$, and $\phi_c$.

Next, a command value transformation unit $5_5$ transforms the command values $x_c$, $\theta_c$, and $\phi_c$ that are found by the command value calculating unit $5_4$, into command values $x_{c1}$, $x_{c2}$, $x_{c3}$, and $x_{c4}$ for the first to fourth piezoelectric devices $4_1$, $4_2$, $4_3$, and $4_4$ respectively. Next, the command value transformation unit $5_5$ corrects the command values $x_{c1}$, $x_{c2}$, $x_{c3}$, and $x_{c4}$ into command values $x_{c1}'$, $x_{c2}'$, $x_{c3}'$, and $x_{c4}'$ using the difference value $\Delta(=|x_2-x_1|)$ between the surface distance $x_1$ between the optical substrates at the position of the first capacitive sensor $3_1$ placed and the surface distance $x_2$ between the optical substrates at the position of the second capacitive sensor $3_2$ placed, the difference value $\Delta$ being calculated by the sensor output transformation unit $5_2$. The corrected command values $x_{c1}'$, $x_{c2}'$, $x_{c3}'$, and $x_{c4}'$ are inputted into a piezoelectric device driver which actuates the first, second, third, and fourth piezoelectric devices $4_1$, $4_2$, $4_3$, and $4_4$ and which is not shown in the drawings, and a actuation voltage is applied to each of the first to fourth piezoelectric devices $4_1$, $4_2$, $4_3$, and $4_4$ by this piezoelectric device driver.

Besides, the command values $x_{c1}$, $x_{c2}$, $x_{c3}$, and $x_{c4}$ for the first to fourth piezoelectric devices $4_1$, $4_2$, $4_3$, and $4_4$ respectively are expressed by the following formulas with known distances $r_{41}$, $r_{42}$, $r_{43}$, and $r_{44}$ to the centers of the first to fourth piezoelectric devices $4_1$, $4_2$, $4_3$, and $4_4$ respectively on the surface of the movable substrate $2_2$:

$$x_{c1}=x_c-r_{41}\sin\theta_c$$

$$x_{c2}=x_c-r_{42}\sin\phi_c$$

$$x_{c3}=x_c+r_{43}\sin\theta_c$$

$$x_{c4}=x_c+r_{44}\sin\phi_c.$$

Also, in the present embodiment, $$r_{41}=r_{42}=r_{43}=r_{44}=r,$$

and, both of the command value $\theta_c$ for the first angle and the command value $\phi_c$ for the second angle are sufficiently small, so that the command values $x_{c1}$, $x_{c2}$, $x_{c3}$, and $x_{c4}$ for the first to fourth piezoelectric devices $4_1$, $4_2$, $4_3$, and $4_4$ respectively are expressed by the following formulas:

$$x_{c1}=x_c-r\theta_c$$

$$x_{c2}=x_c-r\phi_c$$

$$x_{c3}=x_c+r\theta_c$$

$$x_{c4}=x_c+r\phi_c.$$

In this case, the command value transformation unit $5_5$ performs control of correction of deflection of the optical substrate in the variable spectrum element of the present embodiment. That is to say, in the command value transformation unit $5_5$, the command values $x_{c1}$, $x_{c2}$, $x_{c3}$, and $x_{c4}$ for the first to fourth piezoelectric devices $4_1$, $4_2$, $4_3$, and $4_4$ respectively are corrected into the command values $x_{c1}'$, $x_{c2}'$, $x_{c3}'$, and $x_{c4}'$ respectively using the difference value $\Delta(=|x_2-x_1|)$ between the surface distance $x_1$ between the optical substrates at the position of the first capacitive sensor $3_1$ placed and the surface distance $x_2$ between the optical substrates at the position of the second capacitive sensor $3_2$ placed, the difference value $\Delta$ being calculated by the sensor output transformation unit $5_2$, as follows:

$$x_{c1}'=x_c-r\theta_c-(\Delta/2)$$

$$x_{c2}'=x_c-r\phi_c+(\Delta/2)$$

$$x_{c3}'=x_c+r\theta_c-(\Delta/2)$$

$$x_{c4}'=x_c+r\phi_c+(\Delta/2).$$

Afterward, the first to fourth piezoelectric devices $4_1$, $4_2$, $4_3$, and $4_4$ are actuated by the voltages that are applied by the piezoelectric device driver on the basis of the command values $x_{c1}'$, $x_{c2}'$, $x_{c3}'$, and $x_{c4}'$ as corrected with the above-described formulas respectively, so that the movable substrate $2_2$ is moved and the surface distance x between the pair of the optical substrates 2 is changed.

And, in the variable spectrum element of the present embodiment, these control processes performed in the sensor output transformation unit $5_2$, the difference value calculating unit $5_3$, the command value calculating unit $5_4$, and the command value transformation unit $5_5$ respectively and actuations of the first to fourth piezoelectric devices $4_1$, $4_2$, $4_3$, and $4_4$ on the basis of the control processes are repeated until the difference value $\Delta(=|x_2-x_1|)$ approximately becomes equal to zero.

FIGS. 6A and 6B are graphs showing experimental results on the response characteristics of etalon devices when feedback control is performed in each of variable spectrum elements. Besides, a surface distance between the pair of the optical substrates (nm) is plotted on the vertical axis and time (sec) is plotted on the horizontal axis in which FIG. 6A shows an experimental result in a variable spectrum element in the prior art and FIG. 6B shows an experimental result in the variable spectrum element of the present embodiment. Besides, in this experiment, as shown with broken lines, signals are inputted while the target value is being changed every 0.02 seconds.

The diameters of the optical substrates of the etalon devices used in the variable spectrum elements were about 10 mm, and the etalon devices were controlled by giving a command to move the optical substrate while a surface distance of 800 nm and a surface distance of 1000 nm are being alternated with each other every 0.02 seconds.

As seen also from FIGS. 6A and 6B, the surface distance between the pair of the optical substrates of the variable spectrum element of the present embodiment converges to the target value in a considerably shorter time than the surface distance between the optical substrates of the variable spectrum element in the prior art does. As a result, variable spectrum elements of the present invention can change their optical characteristics accurately even in the case where the optical characteristics are changed continuously and at high speed.

In addition, the variable spectrum element of the present embodiment is formed in such a way that the command value transformation unit $5_5$ performs control of the correction of deflection of the optical substrate using the difference value $\Delta$ between the surface distance $x_1$ between the optical substrates at the position of the first capacitive sensor $3_1$ placed and the surface distance $x_2$ between the optical substrates at the position of the second capacitive sensor $3_2$ placed, the difference value $\Delta$ being calculated by the sensor output transformation unit $5_2$. As a result, it is possible to adjust a position of the center of mass of and rotation angles of the optical substrate in consideration for differences between piezoelectric properties of the piezoelectric devices even though there are the differences in piezoelectric properties of the piezoelectric devices on the respective axes.

Now, a difference between the spectral sensitivities due to a difference between: deflection of the optical substrate in the variable spectrum element of the present embodiment including a deflection control means; and deflection of the optical substrate in a variable spectrum element including no deflection control means as described in Japanese Patent TOKU-KAI No. 2011-209574 is explained using test data.

Figure 7:
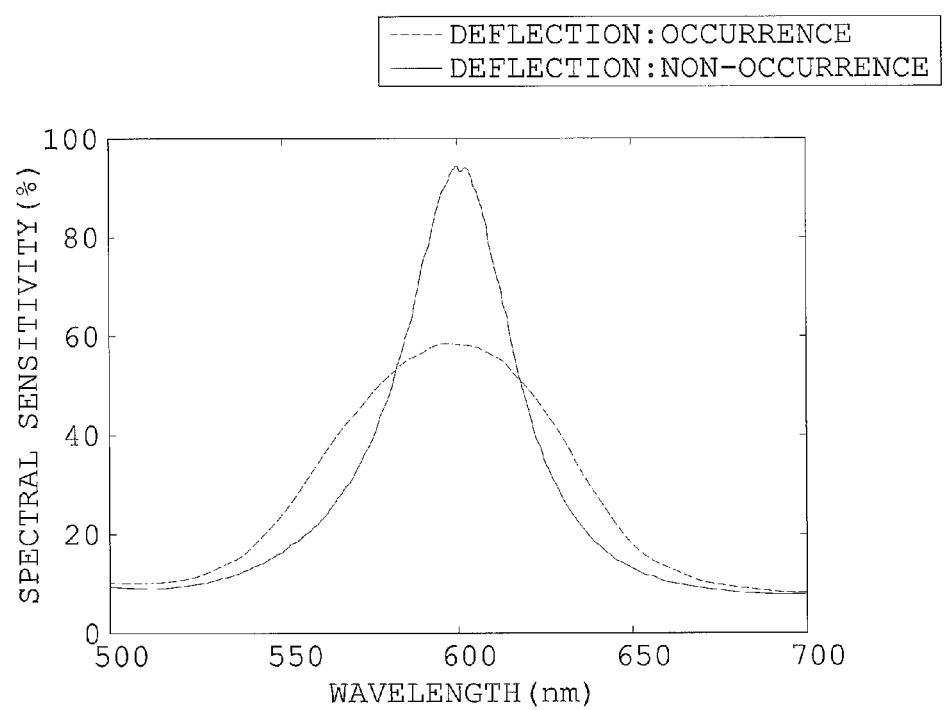
FIG. 7 is a graph showing a spectral sensitivity of the variable spectrum element in which the optical substrate bends and a spectral sensitivity of the variable spectrum element in which the optical substrate does not bend.

FIG. 7 is a graph showing a spectral sensitivity of the variable spectrum element in which the optical substrate bends and a spectral sensitivity of the variable spectrum element in which the optical substrate does not bend.

Optical substrates in which a deflection of about 50 nm could occur were used for the variable spectrum element in which the deflection of the optical substrate occurred, in the data shown in FIG. 7. Also, the variable spectrum element in which deflection of its optical substrate occurred and the variable spectrum element in which deflection of its optical substrate did not occur were put in a setting in which the sensitivities of the variable spectrum elements reached to the maximum at a wavelength of 600 nm.

A deflection amount of about 5 nm occurred when deflection of the optical substrate did not occur, a deflection amount of 50 nm occurred when deflection of the optical substrate occurred, and the etalon devices were controlled so that a surface distance between the optical substrates was kept being 600 nm. The spectral sensitivity characteristics of the variable spectrum elements in this state were measured using an optical spectrum analyzer.

As shown in FIG. 7, the variable spectrum element in which deflection of its optical substrate did not occur had a sharp peak wavelength. On the other hand, a spectral sensitivity deteriorated, a peak wavelength inevitably became horizontally wide, and resolving power also deteriorated in the variable spectrum element in which deflection of its optical substrate occurred.

Accordingly, deflection of an optical substrate cannot be removed from a variable spectrum element that is not provided with any deflection control means as in Japanese Patent TOKUKAI No. 2011-209574, in the case where actuators provided with optical substrates vary in property, so that it is impossible to change its optical characteristics accurately.

On the other hand, the variable spectrum element of the present embodiment includes a deflection control means, so that the variable spectrum element of the present embodiment makes it possible to prevent the occurrence of deflection of its optical substrate even though the properties of actuators in the two directions that are provided for the optical substrates differ from each other. As a result, according to the variable spectrum element of the present embodiment, it is possible to change its optical characteristics at high speed and accurately regardless of whether the properties of actuators in the two directions that are provided for the etalon device differ from each other, or not.

As described above, in the embodiment 1, control of correcting the deflection of the optical substrate is performed using the difference value $\Delta(=|x_2-x_1|)$ between a distance between the surfaces of the pair of the optical substrates 2 opposite to each other at the position of the first piezoelectric device $4_1$ placed and a distance between the surfaces of the pair of the optical substrates 2 opposite to each other at the position of the second piezoelectric device $4_2$ placed. The embodiment 1 provides a constitution in a case where a difference between the properties of actuators opposite to each other is so small that rotation angles of an optical substrate can be controlled high accurately. That is to say, the embodiment 1 provides a constitution applicable to a case where it can be presumed that $x_1 \approx x_3$ and $x_2 \approx x_4$. In order to make a variable spectrum element that is also applicable to a case where it is difficult to control rotation angles of an optical substrate high accurately because of a large difference between the properties of actuators opposite to each other, it is desirable to form the variable spectrum element like a variable spectrum element of the second embodiment which is explained next.

Embodiment 2

Figure 8:
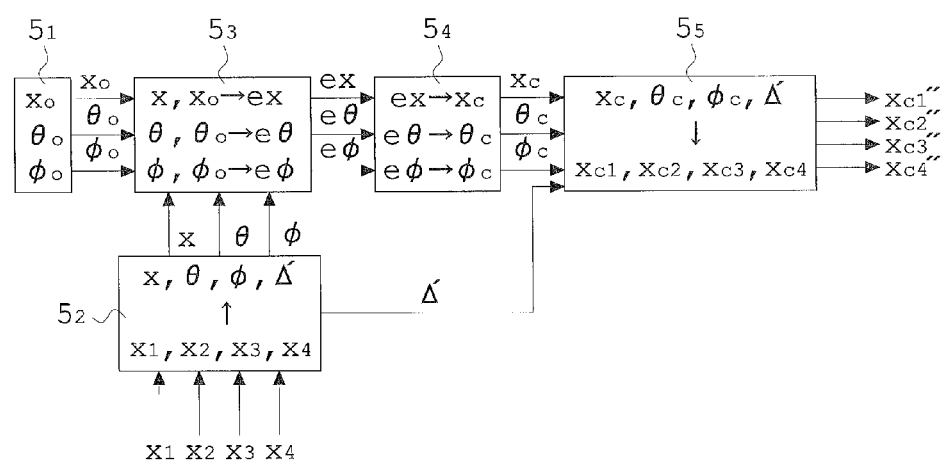
FIG. 8 is a block diagram showing an operation which is performed by a control unit of the variable spectrum element according to an embodiment 2.
Figure 9:
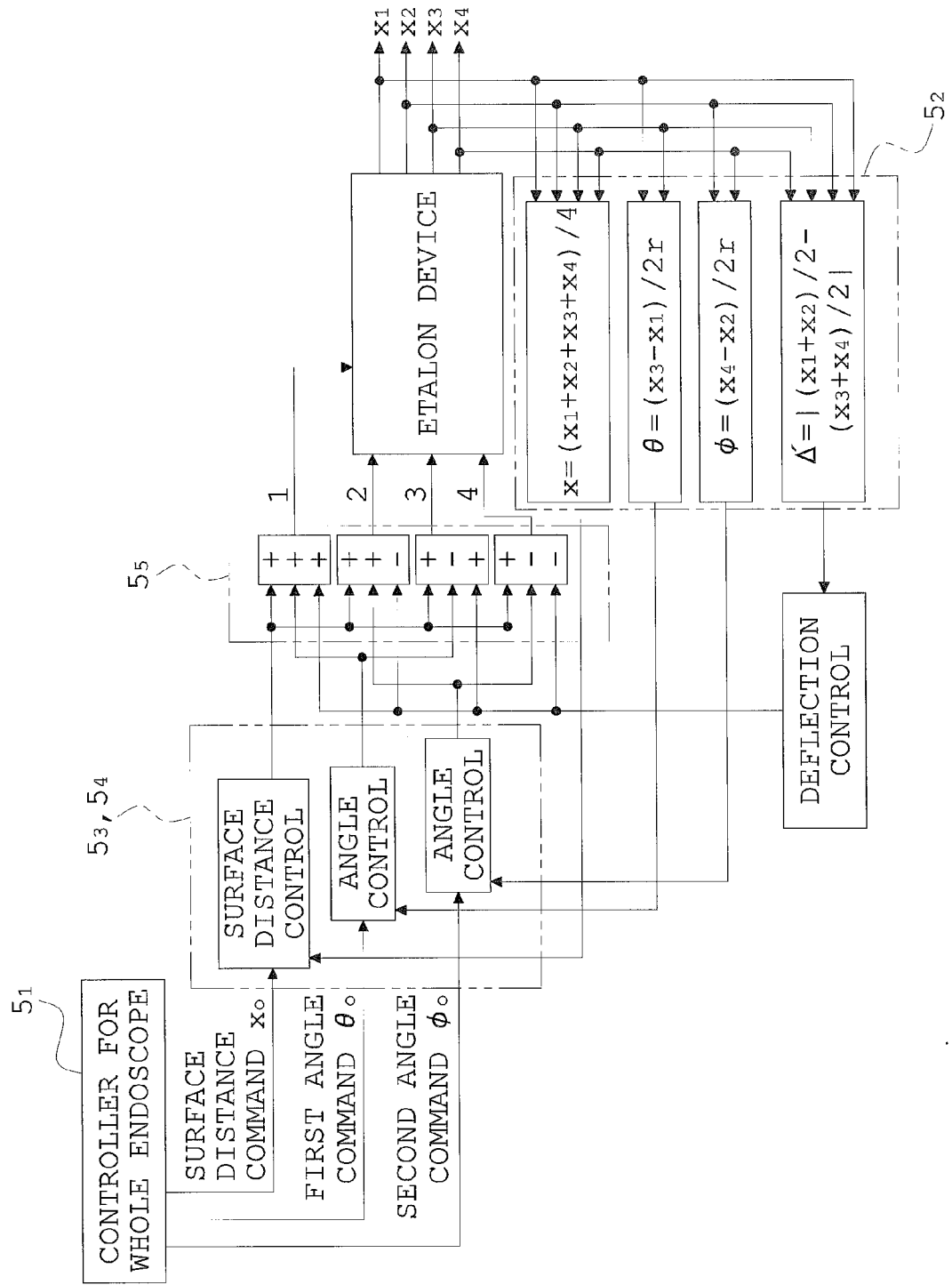
FIG. 9 is a block diagram schematically showing the whole of a structure of control in the variable spectrum element according to the embodiment 2.

FIG. 8 is a block diagram showing an operation which is performed by a control unit of a variable spectrum element according to an embodiment 2. FIG. 9 is a block diagram schematically showing the whole of a structure of control in the variable spectrum element according to the embodiment 2.

The embodiment 2 is an example which is also applicable to the case where it is difficult to control rotation angles of an optical substrate high accurately because of a large difference between surface distances of optical substrates at positions at which actuators opposite to each other are placed.

In the case where a difference between the properties of actuators opposite to each other is large, an accuracy with which rotation angles of the optical substrate are controlled deteriorates. Accordingly, the variable spectrum element of the embodiment 2 is formed to perform control of deflection of the optical substrate using a difference between: the average of distances between the surfaces of the optical substrates at the positions at which actuators opposite to each other in the first direction are placed; and the average of distances between the surfaces of the optical substrates at the positions at which actuators opposite to each other in the second direction are placed. Besides, an etalon device for the embodiment 2 has the same constitution as that of the etalon device for the embodiment 1 shown in FIGS. 1 to 3.

In a detailed explanation, in the variable spectrum apparatus of the embodiment 2 as shown in FIGS. 8 and 9, after a target value $\theta_0$ of a first angle and a target value $\phi_0$ of a second angle are inputted into the control unit through a target value input unit $5_1$, a sensor output transformation unit $5_2$ acquires surface distances $x_1$, $x_2$, $x_3$, and $x_4$ between the pair of the optical substrates 2 at the positions at which the first, second, third, and fourth capacitive sensors $3_1$, $3_2$, $3_3$, and $3_4$ are placed respectively, the surface distances $x_1$, $x_2$, $x_3$, and $x_4$ at the respective positions being measured by these capacitive sensors $3_1$, $3_2$, $3_3$, and $3_4$ respectively. And then, the sensor output transformation unit $5_2$ not only calculates a difference value $\Delta'(=|(x_1+x_3)/2-(x_2+x_4)/2|)$ between: the average $(x_1+x_3)/2$ of the surface distances $x_1$ and $x_3$ between the optical substrates; and the average $(x_2+x_4)/2$ of the surface distances $x_2$ and $x_4$ between the optical substrates but also transforms the surface distances $x_1$, $x_2$, $x_3$, and $x_4$ into the current value x of a distance between the centers of mass $G_1$ and $G_2$, the current value $\theta$ of the first angle, and the current value $\phi$ of the second angle.

Also, after a difference value calculating unit $5_3$ calculates difference values ex, e$\theta$, and e$\phi$ and the command value calculating unit $5_4$ finds command values $x_c$, $\theta_c$, and $\phi_c$, a command value transformation unit $5_5$ transforms the command values $x_c$, $\theta_c$, and $\phi_c$ that are found by the command value calculating unit $5_4$, into command values $x_{c1}$, $x_{c2}$, $x_{c3}$, and $x_{c4}$ for the first to fourth piezoelectric devices $4_1$, $4_2$, $4_3$, and $4_4$ respectively. Next, the command value transformation unit $5_5$ corrects the command values $x_{c1}$, $x_{c2}$, $x_{c3}$, and $x_{c4}$ into command values $x_{c1}''$, $x_{c2}''$, $x_{c3}''$, and $x_{c4}''$ using the difference value $\Delta'(=|(x_1+x_3)/2-(x_2+x_4)/2|)$ between: the average of the surface distance $x_1$ between the optical substrates at the position of the first capacitive sensor $3_1$ placed and the surface distance $x_3$ between the optical substrates at the position of the third capacitive sensor $3_3$ placed; and the average of the surface distance $x_2$ between the optical substrates at the position of the second capacitive sensor $3_2$ placed and the surface distance $x_4$ between the optical substrates at the position of the fourth capacitive sensor $3_4$ placed, the difference value $\Delta'$ being calculated by the sensor output transformation unit $5_2$. The corrected command values $x_{c1}''$, $x_{c2}''$, $x_{c3}''$, and $x_{c4}''$ are inputted into a piezoelectric device driver which actuates the first, second, third, and fourth piezoelectric devices $4_1$, $4_2$, $4_3$, and $4_4$ and which is not shown in the drawings, and a actuation voltage is applied to each of the first to fourth piezoelectric devices $4_1$, $4_2$, $4_3$, and $4_4$ by this piezoelectric device driver.

Besides, the command values $x_{c1}$, $x_{c2}$, $x_{c3}$, and $x_{c4}$ for the first to fourth piezoelectric devices $4_1$, $4_2$, $4_3$, and $4_4$ respectively are expressed by the following formulas with known distances $r_{41}$, $r_{42}$, $r_{43}$, and $r_{44}$ to the centers of the first to fourth piezoelectric devices $4_1$, $4_2$, $4_3$, and $4_4$ respectively on the surface of the movable substrate $2_2$:

$$x_{c1}=x_c-r_{41}\sin\theta_c$$

$$x_{c2}=x_c-r_{42}\sin\phi_c$$

$$x_{c3}=x_c+r_{43}\sin\theta_c$$

$$x_{c4}=x_c+r_{44}\sin\phi_c.$$

Also in the embodiment 2, $$r_{41}=r_{42}=r_{43}=r_{44}=r,$$

and, both of the command value $\theta_0$ for the first angle and the command value $\phi_c$ for the second angle are sufficiently small, so that the command values $x_{c1}$, $x_{c2}$, $x_{c3}$, and $x_{c4}$ for the first to fourth piezoelectric devices $4_1$, $4_2$, $4_3$, and $4_4$ respectively are expressed by the following formulas:

$$x_{c1}=x_c-r\theta_c$$

$$x_{c2}=x_c-r\phi_c$$

$$x_{c3}=x_c+r\theta_c$$

$$x_{c4}=x_c+r\phi_c.$$

In this case, the command value transformation unit $5_5$ performs control of correction of deflection of the optical substrate in the variable spectrum element of the embodiment 2. That is to say, in the command value transformation unit $5_5$, the command values $x_{c1}$, $x_{c2}$, $x_{c3}$, and $x_{c4}$ for the first to fourth piezoelectric devices $4_1$, $4_2$, $4_3$, and $4_4$ respectively are corrected into command values $x_{c1}''$, $x_{c2}''$, $x_{c3}''$, and $x_{c4}''$ respectively using the difference value $\Delta'(=|(x_1+x_3)/2-(x_2+x_4)/2|)$ between: the average of the surface distance $x_1$ between the optical substrates at the position of the first capacitive sensor $3_1$ placed and the surface distance $x_3$ between the optical substrates at the position of the third capacitive sensor $3_3$ placed; and the average of the surface distance $x_2$ between the optical substrates at the position of the second capacitive sensor $3_2$ placed and the surface distance $x_4$ between the optical substrates at the position of the fourth capacitive sensor $3_4$ placed, the difference value $\Delta'$ being calculated by the sensor output transformation unit $5_2$, as follows:

$$x_{c1}''=x_c-r\theta_c-(\Delta'/2)$$

$$x_{c2}''=x_c-r\phi_c+(\Delta'/2)$$

$$x_{c3}''=x_c+r\theta_c-(\Delta'/2)$$

$$x_{c4}''=x_c+r\phi_c+(\Delta'/2).$$

Afterward, the first to fourth piezoelectric devices $4_1$, $4_2$, $4_3$, and $4_4$ are actuated by the voltages that are applied by the piezoelectric device driver on the basis of the command values $x_{c1}''$, $x_{c2}''$, $x_{c3}''$, and $x_{c4}''$ as corrected with the above-described formulas respectively, so that the movable substrate $2_2$ is moved and the surface distance x between the pair of the optical substrates 2 is changed.

And, in the variable spectrum element of the embodiment 2, these control processes performed in the sensor output transformation unit $5_2$, the difference value calculating unit $5_3$, the command value calculating unit $5_4$, and the command value transformation unit $5_5$ respectively and actuations of the first to fourth piezoelectric devices $4_1$, $4_2$, $4_3$, and $4_4$ on the basis of the control processes are repeated until the difference value $\Delta'(=|(x_1+x_3)/2-(x_2+x_4)/2|)$ approximately becomes equal to zero.

According to the variable spectrum element of the embodiment 2, it is possible to control rotation angles of its optical substrate high accurately even in the case where a difference between the properties of actuators opposite to each other is large, so that it is possible to change its optical characteristics more accurately in the variable spectrum element of the embodiment 2 in addition to the fact that the variable spectrum element of the embodiment 2 has the effects of the variable spectrum element of the embodiment 1.

Embodiment 3

Figure 10:
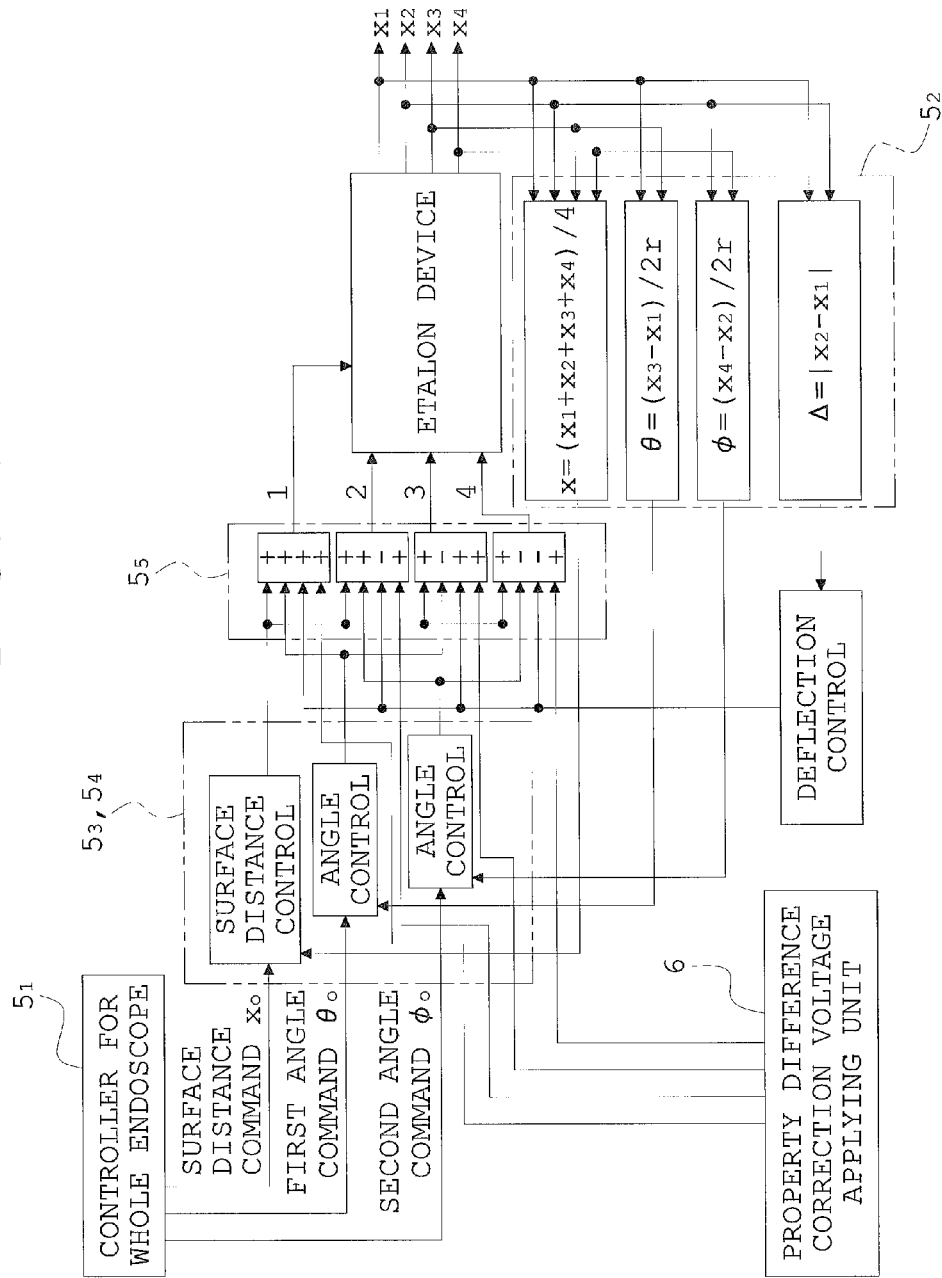
FIG. 10 is a block diagram schematically showing the whole of a structure of control in the variable spectrum element according to an embodiment 3.

FIG. 10 is a block diagram schematically showing the whole of a structure of control in a variable spectrum element according to an embodiment 3.

The variable spectrum element of the embodiment 3 has not only the structure of the variable spectrum element of the embodiment 1 but also includes a property difference correction voltage applying unit 6 by which an offset voltage for cancelling differences between the properties of first to fourth actuators is applied to each of the first to fourth actuators in operating a variable control unit 5.

The property difference correction voltage applying unit 6 is composed of, for example, a ROM (which is not shown in the drawings), the ROM storing fixed values of offset voltages which are set in advance in order to cancel differences between the piezoelectric properties of the first to fourth piezoelectric devices $4_1$, $4_2$, $4_3$, and $4_4$. And, a predetermined offset voltage is applied to each of channels for the first to fourth piezoelectric devices $4_1$, $4_2$, $4_3$, and $4_4$ by the property difference correction voltage applying unit 6, in operating the control unit 5.

Alternatively, for example, the property difference correction voltage applying unit 6 may be formed: to be composed of not only the above-described ROM but also a temperature-humidity sensor (which is not shown in the drawings) and a so-called lookup table (which is not shown in the drawings) in which information on temperature and humidity is used as a key and which stores data on offset voltages according to the actuation characteristics of the first to fourth piezoelectric devices $4_1$, $4_2$, $4_3$, and $4_4$ (amounts of the first to fourth piezoelectric devices $4_1$, $4_2$, $4_3$, and $4_4$ expanding or contracting to input voltages); and to be operate in such a way that a offset voltage applied to each of the channels for the first to fourth piezoelectric devices $4_1$, $4_2$, $4_3$, and $4_4$ is changed in accordance with information on temperature and humidity which is detected by the temperature-humidity sensor in real time, in operating the control unit 5.

In the variable spectrum element of the embodiment 3, the property difference correction voltage applying unit 6 reduce differences between the properties of the first to fourth piezoelectric devices $4_1$, $4_2$, $4_3$, and $4_4$ to the utmost in operating the control to unit 5, the first to fourth piezoelectric devices $4_1$, $4_2$, $4_3$, and $4_4$ being the first to fourth actuators respectively, so that it is possible to reduce operation loads for the control unit 5. As a result, the variable spectrum element of the embodiment 3 not only has the effects of the spectroscopic element of the embodiment 1 but also makes it possible to change its optical characteristics at the higher speed and the higher accurately.

And, when the property difference correction voltage applying unit 6 is composed of a ROM which stores fixed values of offset voltages (and which is not shown in the drawings), the structure of the property difference correction voltage applying unit 6 can be simplified. Also, when the property difference correction voltage applying unit 6 is formed so that offset voltages are changed from one another in real time, it is also possible to deal with variations in the properties of the piezoelectric devices which are caused by environmental changes or chronological change, so that it is possible to change its optical characteristics high accurately.

The other operation effects of the variable spectrum element of the embodiment 3 are almost the same as those of the variable spectrum element of the embodiment 1.

Embodiment 4

Figure 11:
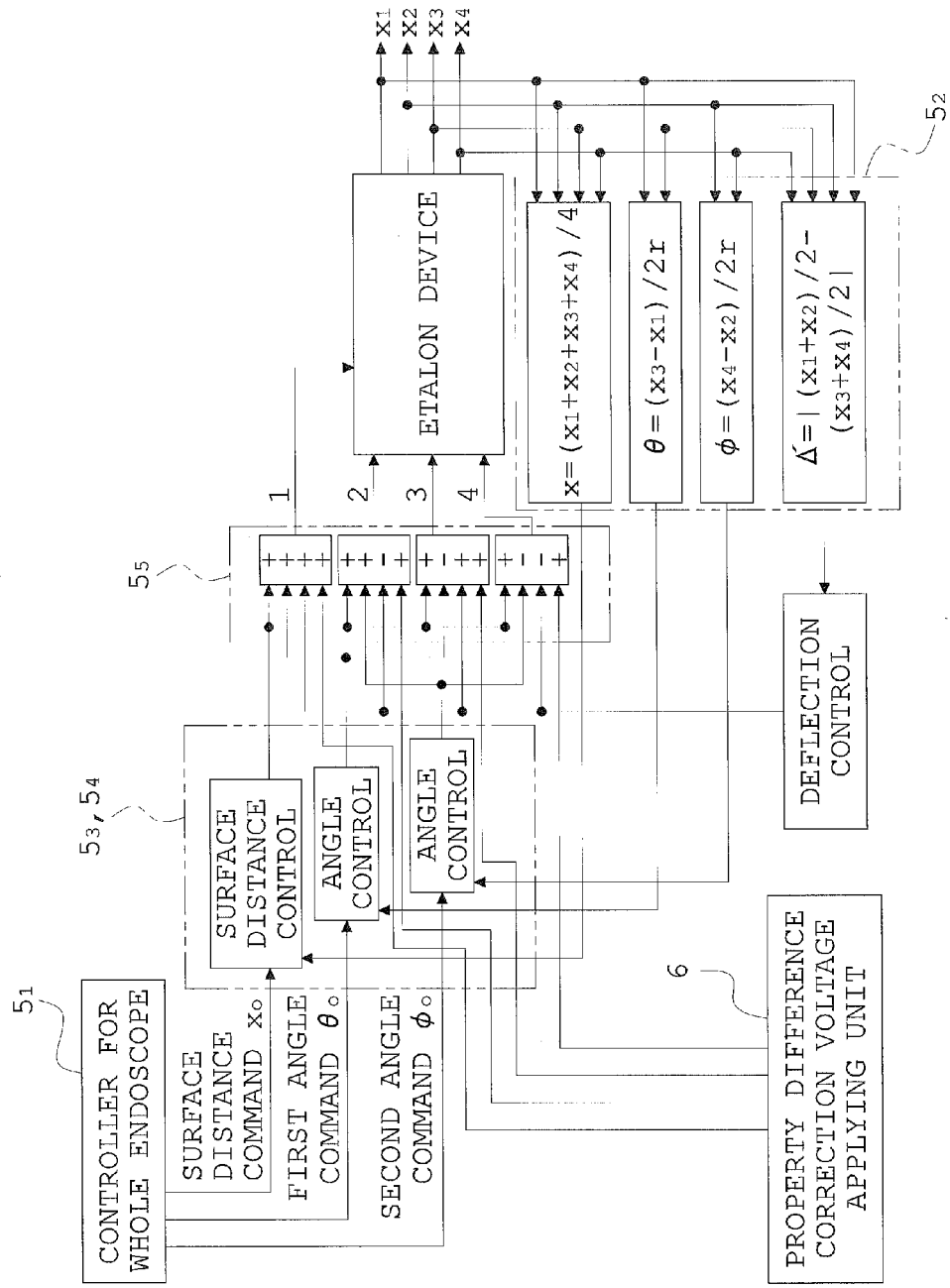
FIG. 11 is a block diagram schematically showing the whole of a structure of control in the variable spectrum element according to an embodiment 4.

FIG. 11 is a block diagram schematically showing the whole of a structure of control in the variable spectrum element according to an embodiment 4.

The variable spectrum element of the embodiment 4 includes not only the constitution of the variable spectrum element of the embodiment 2 but also a property difference correction voltage applying unit 6 by which an offset voltage for cancelling differences between the properties of first to fourth actuators is applied to each of the first to fourth actuators in operating the control unit 5.

The constitution of the property difference correction voltage applying unit 6 is almost the same as that that of the property difference correction voltage applying unit provided for the variable spectrum element of the embodiment 3.

In the variable spectrum element of the embodiment 4, the property difference correction voltage applying unit 6 reduce differences between the properties of the first to fourth piezoelectric devices $4_1$, $4_2$, $4_3$, and $4_4$ to the utmost in operating the control unit 5, the first to fourth piezoelectric devices $4_1$, $4_2$, $4_3$, and $4_4$ being the first to fourth actuators respectively, so that it is possible to reduce operation loads for the control unit 5. As a result, the variable spectrum element of the embodiment 4 not only has the effects of the spectroscopic element of the embodiment 2 but also makes it possible to change its optical characteristics at the higher speed and the higher accurately. In particular, the variable spectrum element of the embodiment 4 is effective in the case where differences between the properties of the first to fourth piezoelectric devices $4_1$, $4_2$, $4_3$, and $4_4$ are large and it is difficult to control rotation angles of an optical substrate.

And, when the property difference correction voltage applying unit 6 is composed of a ROM which stores fixed values of offset voltages (and which is not shown in the drawings), the structure of the property difference correction voltage applying unit 6 can be simplified. Also, when the property difference correction voltage applying unit 6 is formed to operate in such a way that offset voltages are changed from one another in real time, it is also possible to deal with variations in the properties of the piezoelectric devices which are caused by environmental changes or chronological change, so that it is possible to change its optical characteristics high accurately.

The other operation effects of the variable spectrum element of the embodiment 4 are almost the same as those of the variable spectrum element of the embodiment 2.

Next, examples of variations of the etalon device for the variable spectrum elements of the above-described embodiments are explained using FIGS. 12 to 15.

Figure 12:
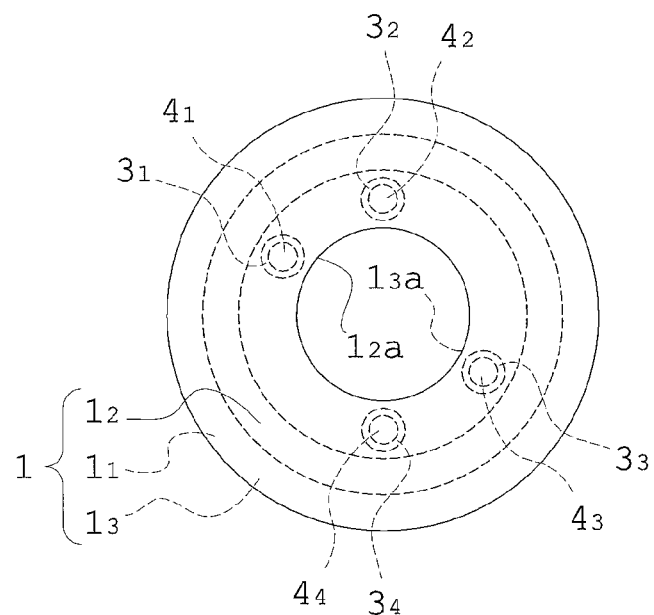
FIG. 12 is a plane view showing the first example of variations of the etalon device shown in FIG. 1.
Figure 13:
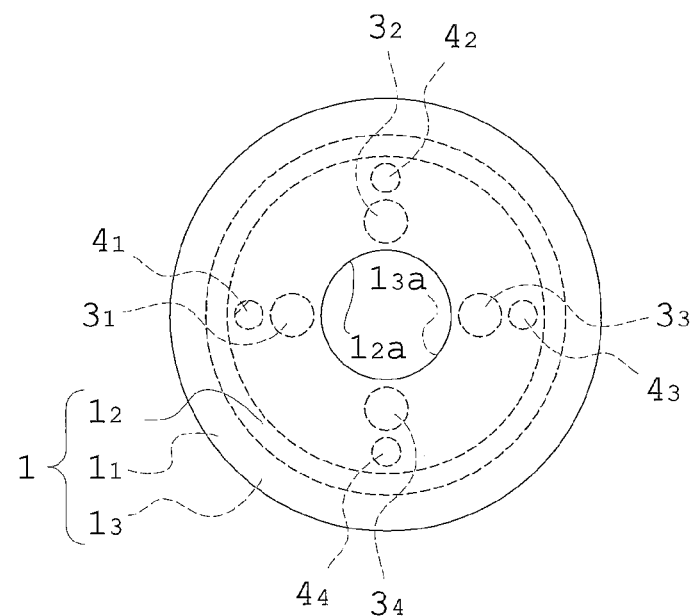
FIG. 13 is a plane view showing the second example of variations of the etalon device shown in FIG. 1.
Figure 14:
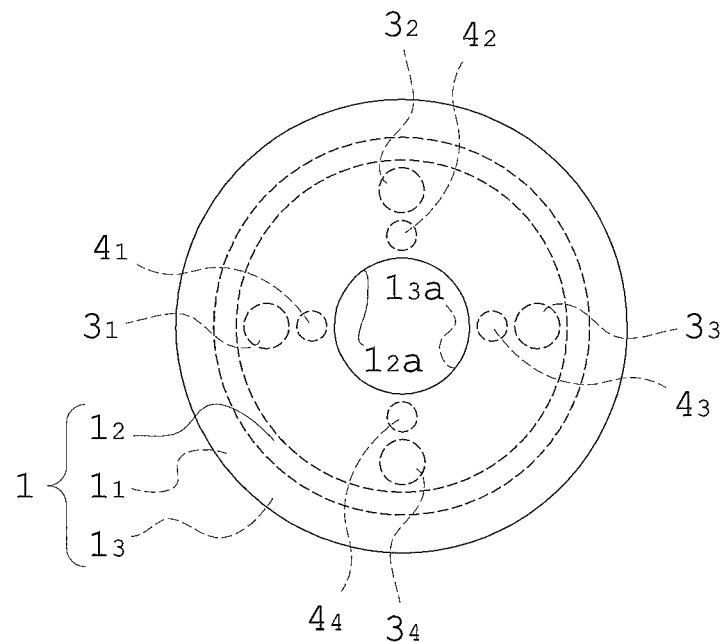
FIG. 14 is a plane view showing the third example of variations of the etalon device shown in FIG. 1.
Figure 15:
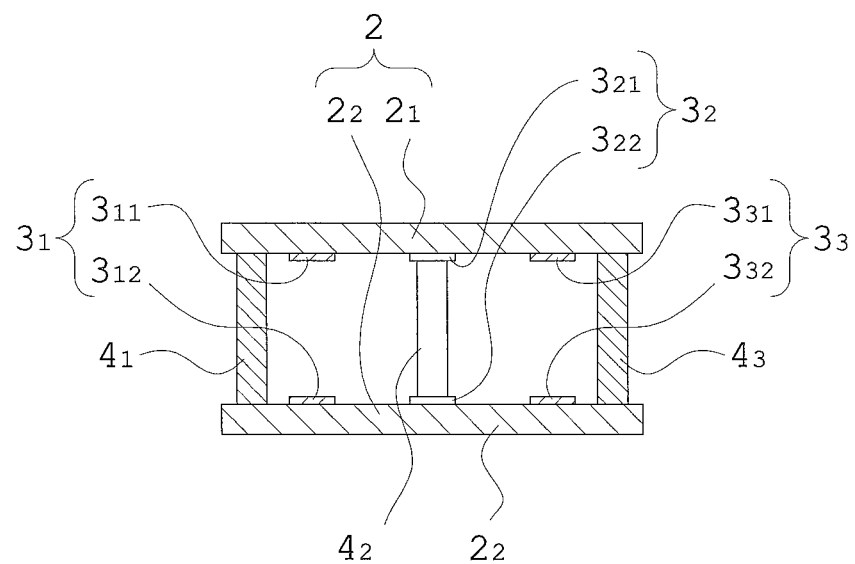
FIG. 15 is a plane view showing the fourth example of variations of the etalon device shown in FIG. 1.

FIG. 12 is a plane view showing a first example of variations of the etalon device shown in FIG. 1. FIG. 13 is a plane view showing a second example of variations of the etalon device shown in FIG. 1. FIG. 14 is a plane view showing a third example of variations of the etalon device shown in FIG. 1. FIG. 15 is a cross sectional view showing a fourth example of variations of the etalon device shown in FIG. 1.

In the etalon device shown in FIG. 12 unlike the etalon device for the variable spectrum elements of the above-described embodiments, the first capacitive sensor $3_1$ and the first piezoelectric device $4_1$, the second capacitive sensor $3_2$ and the second piezoelectric device $4_2$, the third capacitive sensor $3_3$ and the third piezoelectric device $4_3$, and the fourth capacitive sensor $3_4$ and the fourth piezoelectric device $4_4$ are not arranged at regular interval when these capacitive sensors and these piezoelectric devices are viewed from the direction along the line connecting the centers of mass of the surfaces of the pair of the optical substrates 2 opposite to each other.

However, the first capacitive sensor $3_1$, the third capacitive sensor $3_3$, the first piezoelectric device $4_1$, and the third piezoelectric device $4_3$ are arranged at positions at which the first capacitive sensor $3_1$ and the first piezoelectric device $4_1$ are symmetrical to the third capacitive sensor $3_3$ and the third piezoelectric device $4_3$ with respect to the line connecting the centers of mass of the surfaces of the pair of the optical substrates 2 opposite to each other when these capacitive sensors and these piezoelectric devices are viewed from the direction along the line connecting the centers of mass of the surfaces of the pair of the optical substrates 2, respectively, and the second capacitive sensor $3_2$, the fourth capacitive sensor $3_4$, the second piezoelectric device $4_2$, and the fourth piezoelectric device $4_4$ are arranged at positions at which the second capacitive sensor $3_2$ and the second piezoelectric device $4_2$ are symmetrical to the fourth capacitive sensor $3_4$ and the fourth piezoelectric device $4_4$ with respect to the line connecting the centers of mass of the surfaces of the pair of the optical substrates 2 opposite to each other when these capacitive sensors and these piezoelectric devices are viewed from the direction along the line connecting the centers of mass of the surfaces of the pair of the optical substrates 2, respectively, so that it is possible to perform control of the etalon devices by performing the same operations as are performed in the variable spectrum elements of the above-described embodiments, through the control unit, even though these capacitive sensors and these piezoelectric devices are arranges in such a manner.

In etalon devices shown in FIGS. 13 and 14 respectively unlike the etalon device for the variable spectrum elements of the above-described embodiments, the first, second, third, and fourth capacitive sensors $3_1$, $3_2$, $3_3$, and $3_4$ and the first, second, third, and fourth piezoelectric devices $4_1$, $4_2$, $4_3$, and $4_4$ are arranged at positions at which the first piezoelectric device $4_1$ does not overlap with the first capacitive sensor $3_1$, the second piezoelectric device $4_2$ does not overlap with the second capacitive sensor $3_2$, the third piezoelectric device $4_3$ does not overlap with the third capacitive sensor $3_3$, and the fourth piezoelectric device $4_4$ does not overlap with the fourth capacitive sensor $3_4$ when these capacitive sensors and these piezoelectric devices are viewed from the direction along the line connecting the centers of mass of the surfaces of the pair of the optical substrates 2 opposite to each other, respectively.

However, the first, second, third, and fourth piezoelectric devices $4_1$, $4_2$, $4_3$, and $4_4$ are arranged on the lines running to the centers of the first, second, third, and fourth capacitive sensors $3_1$, $3_2$, $3_3$, and $3_4$ respectively, respectively when these capacitive sensors and these piezoelectric devices are viewed from the direction along the line connecting the centers of mass of the surfaces of the pair of the optical substrates 2 opposite to each other, so that it is possible to perform control of the etalon devices by performing the same operation as are performed in the variable spectrum elements of the above-described embodiments, through the control unit, even though these capacitive sensors and these piezoelectric devices are arranged in such a manner.

Unlike the etalon device for the variable spectrum elements of the above described embodiments, the etalon device shown in FIG. 15 is not provided with the outer flame 1, and the first piezoelectric device $4_1$, the second piezoelectric device $4_2$, the third piezoelectric device $4_3$, and the fourth piezoelectric device $4_4$ are fixed on the surface of the fixed substrate $2_1$ opposite to the other substrate with the first, second, third and fourth piezoelectric devices not intercepting light passing through the etalon device.

However, even though the etalon device shown in FIG. 15 has such a constitution, it is possible to perform control of the etalon devices by performing the same operations as are performed in the variable spectrum elements of the above-described embodiments, through the control unit.

Embodiment 5

Figure 16:
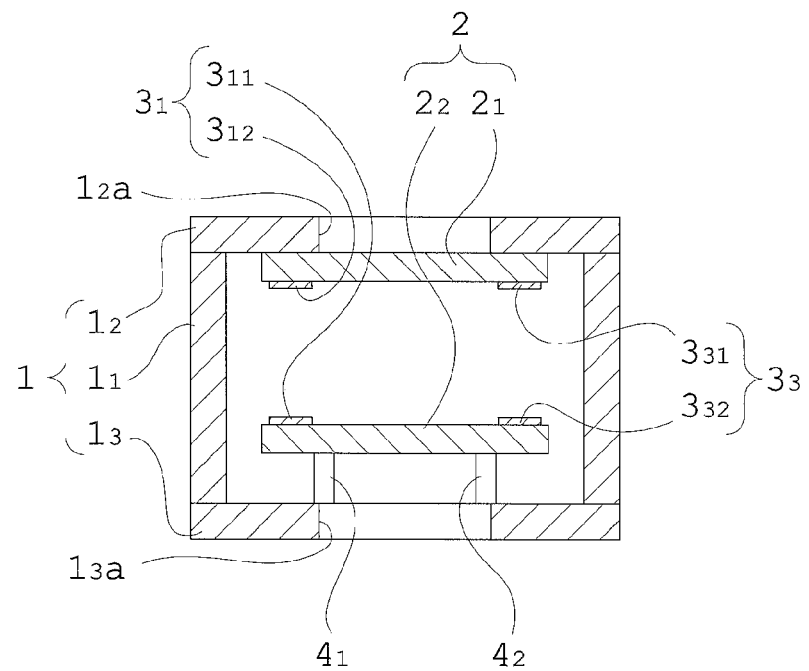
FIG. 16 is a cross sectional view showing an etalon device in a variable spectrum element according to an embodiment 5.
Figure 17:
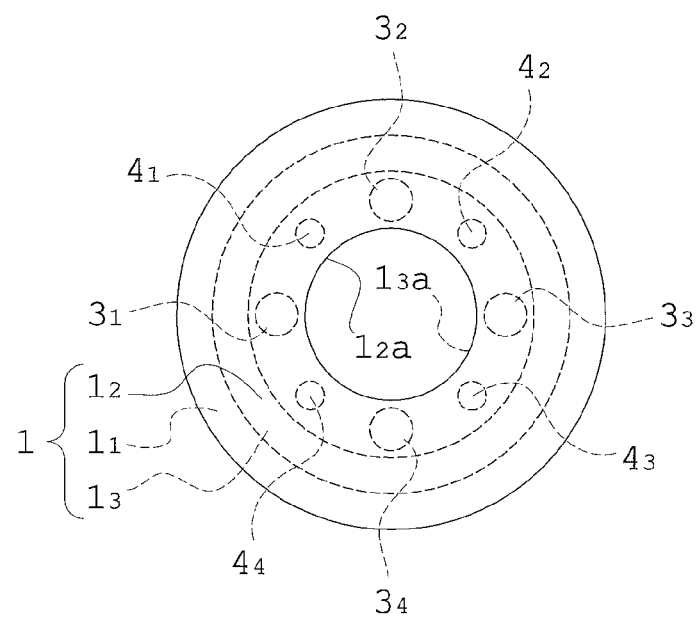
FIG. 17 is a plane view showing the etalon device shown in FIG. 16.

A variable spectrum element of the embodiment 5, which is a variable spectrum element according to the present invention and is provided with an etalon device, is explained using FIGS. 16 and 17. Besides, because components constituting a etalon device for the variable spectrum element of the embodiment 5 are the same as those constituting the etalon device for the variable spectrum element of the embodiment 1, components having the same structure as in the embodiment 1 are given the same numeral reference as in the embodiment 1, and detailed explanations about these components are omitted. Also, because the structure of a control unit and operations performed by the control unit in the variable spectrum element of the embodiment 5 are almost the same as those in the variable spectrum element of the embodiment 1, detailed explanations about these matters are omitted.

Besides, FIG. 16 is a cross sectional view showing the etalon device in a variable spectrum element according to the present embodiment. FIG. 17 is a plane view showing the etalon device shown in FIG. 16.

The constitution of the etalon device for this variable spectrum element is explained using FIGS. 16 and 17.

In the etalon device for the variable spectrum element of the embodiment 5 unlike the etalon device for the variable spectrum element of the embodiment 1, the first, second, third, and fourth capacitive sensors $3_1$, $3_2$, $3_3$, and $3_4$ and the first, second, third, and fourth piezoelectric devices $4_1$, $4_2$, $4_3$, $4_4$ are arranged in a circle at regular intervals while the first, second, third, and fourth piezoelectric devices $4_1$, $4_2$, $4_3$, and $4_4$ are alternating with the first, second, third, and fourth capacitive sensors $3_1$, $3_2$, $3_3$, and $3_4$ when these capacitive sensors and these piezoelectric devices are viewed from the direction along the line connecting the centers of mass of the surfaces of the pair of the optical substrates 2 opposite to each other.

Next, actuation of the movable substrate $2_2$ in the etalon device for the variable spectrum element of the embodiment 5 and control of actuation of the movable substrate $2_2$ are explained.

In the variable spectrum element of the embodiment 1, a distance x between the centers of mass of the surfaces of the pair of the optical substrates 2 opposite to each other is found with output values from the first, second, third, and fourth capacitive sensors $3_1$, $3_2$, $3_3$, and $3_4$, a first angle θ is found with output values from the first and third capacitive sensors $3_1$ and $3_3$, and a second angle ϕ is found with output values from the second and fourth capacitive sensors $3_2$ and $3_4$. And, actuations of the first and third piezoelectric devices $4_1$, and $4_3$ are controlled on the basis of the distance x between the centers of mass of the surfaces of the optical substrates 2 and the first angle θ, and actuations of the second and fourth piezoelectric devices $4_2$, and $4_4$ are controlled on the basis of the distance x between the centers of mass of the surfaces of the optical substrates 2, the second angle ϕ, and a difference value Δ between: a distances $x_1$ between the surfaces of the optical substrates at the position of the first capacitive sensor $3_1$ placed; and a distance $x_2$ between the surfaces of the optical substrates at the position of the second capacitive sensor $3_2$ placed.

On the other hand, in the variable spectrum element of the embodiment 5, a distance x between the centers of mass of the surfaces of the optical substrates is found and surface distances $x_{41}$, $x_{42}$, $x_{43}$, and $x_{44}$ between the pair of the optical substrates 2 at the positions at which the first, second, third, and fourth piezoelectric devices $4_1$, $4_2$, $4_3$, and $4_4$ are placed on the pair of the optical substrates respectively are found, with all of the output values from the first, second, third, and fourth capacitive sensors $3_1$, $3_2$, $3_3$, and $3_4$. And then, a first angle θ and a second angle ϕ are found with the found surface distances $x_{41}$, $x_{42}$, $x_{43}$, and $x_{44}$. And then, as in the variable spectrum element of the embodiment 1, actuations of the first, second, third, and fourth piezoelectric devices $4_1$, $4_2$, $4_3$, and $4_4$ are controlled on the basis of the distance x between the centers of mass of the surfaces of the optical substrates, the first angle θ, the second angle ϕ, and a difference value $\Delta(=|x_{42}-x_{41}|)$ between a distances $x_{41}$ between the surfaces of the optical substrates at the position of the first piezoelectric device $4_1$ placed and a distance $x_{42}$ between the surfaces of the optical substrates at the position of the second piezoelectric device $4_2$ placed. Alternatively, as in the variable spectrum element of the embodiment 2, actuations of the first, second, third, and fourth piezoelectric devices $4_1$, $4_2$, $4_3$, and $4_4$ are controlled on the basis of the distance x between the centers of mass of the surfaces of the optical substrates, the first angle θ, the second angle ϕ, and a difference value $\Delta'(=|(x_{41}+x_{43})/2-(x_{42}+x_{44})/2|)$ between: the average of a distances $x_{41}$ between the surfaces of the optical substrates at the position of the first piezoelectric device $4_1$ placed and a distance $x_{43}$ between the surfaces of the optical substrates at the position of the third piezoelectric device $4_3$ placed; and the average of a distances $x_{42}$ between the surfaces of the optical substrates at the position of the second piezoelectric device $4_2$ placed and a distance $x_{44}$ between the surfaces of the optical substrates at the position of the fourth piezoelectric device $4_4$ placed.

As described above, although the capacitive sensors 3 and the corresponding piezoelectric devices 4 are not placed at the positions at which the capacitive sensors 3 overlap with the corresponding piezoelectric devices 4 respectively when these capacitive sensors and these piezoelectric devices are viewed from the direction along the line connecting the centers of mass of the surfaces of the pair of the optical substrates 2 opposite to each other, in the variable spectrum element of the embodiment 5, the distances $x_1$, $x_2$, $x_3$, and $x_4$ between the surfaces of the pair of the optical substrates 2 opposite to each other, which are detected by the capacitive sensors 3, are transformed into the distances $x_{41}$, $x_{42}$, $x_{43}$, and $x_{44}$ between the surfaces of the optical substrates 2 at the positions of the first, second, third, and fourth piezoelectric devices $4_1$, $4_2$, $4_3$, and $4_4$ placed respectively. As a result, it is possible to perform the same control as in the embodiment 1, in the embodiment 5.

Accordingly, also in the embodiment 5 as in the variable spectrum element of the embodiment 1, a distance between the surfaces of the pair of the optical substrates 2 converges in a considerably shorter time than in the cases of variable spectrum elements in the prior art. As a result, the variable spectrum element of the embodiment 5 can change its optical characteristics accurately even though its optical characteristics are changed continuously and at high speed.

In addition, in the embodiment 5, the command value transformation unit $5_5$ performs control of deflection of the optical substrate using a difference value $\Delta(=|x_{42}-x_{41}|)$ between the surface distances $x_{41}$ between the optical substrates 2 at the positions of the first piezoelectric device $4_1$ placed and the surface distance $x_{42}$ between the optical substrates 2 at the position of the second piezoelectric device $4_2$ placed or using a difference value $\Delta'(=|(x_{41}+x_{43})/2-(x_{42}+x_{44})/2|)$ between: the average of the surface distances $x_{41}$ between the optical substrates at the positions of the first piezoelectric device $4_1$ placed and the surface distance $x_{43}$ between the optical substrates at the position of the third piezoelectric device $4_3$ placed; and the average of the surface distances $x_{42}$ between the optical substrates at the positions of the second piezoelectric device $4_2$ placed and the surface distance $x_{44}$ between the optical substrates at the position of the fourth piezoelectric device $4_4$ placed, the difference values Δ and Δ' being calculated by the sensor output transformation unit $5_2$. As a result, even though there exist differences between the piezoelectric properties of the actuators on the respective axes, it is possible to adjust a position of the center of mass and angles to values for which the differences are taken into consideration.

Accordingly, the variable spectrum element of the embodiment 5 makes it possible to change its optical characteristics at high speed and accurately even though there exists a difference between actuators in the two directions in property, the actuators being provided for an etalon.

What is claimed is:

1. A variable spectrum element comprising
   a pair of optical substrates arranged opposite at a distance from each other,
   first, second, third, and fourth capacitive sensors each including a pair of electrodes that are placed on surfaces of the pair of the optical substrates opposite to each other respectively and each detecting a distance between the surfaces of the pair of the optical substrates opposite to each other at each placed position, and
   first, second, third, and fourth actuators relatively moving one of the pair of the optical substrates relative to the other optical substrate to change a distance between the surfaces of the pair of the optical substrates opposite to each other,
   the first and third capacitive sensors being placed at positions at which the first and third capacitive sensors are symmetrical with respect to a line connecting centers of mass of the surfaces of the pair of the optical substrates opposite to each other, respectively, the second and fourth capacitive sensors being placed at positions at which the second and fourth capacitive sensors are symmetrical with respect to the line connecting the centers of mass of the surfaces of the pair of the optical substrates opposite to each other, respectively, the first, second, third, and fourth actuators being placed on lines running from the center of mass of the surface of each of the pair of the optical substrates opposite to each other to the centers of the first, second, third, and fourth capacitive sensors respectively, respectively, and the variable spectrum element comprising a control unit, the control unit calculating a distance between the centers of mass of the surfaces of the pair of the optical substrates opposite to each other, with signals from the first, second, third, and fourth capacitive sensors, the control unit calculating a first angle that is made between a surface perpendicular to the line connecting the centers of mass of the surfaces of the pair of the optical substrates and the surface of the relatively moved optical substrate of the surfaces of the pair of the optical substrates opposite to each other, with signals from the first and third capacitive sensors, the control unit calculating a second angle that is made between the surface perpendicular to the line connecting the centers of mass of the surfaces of the pair of the optical substrates and the surface of the relatively moved optical substrate of the surfaces of the pair of the optical substrates opposite to each other, with signals from the second and fourth capacitive sensors, the control unit calculating a difference between a distance between the surfaces of the pair of the optical substrates opposite to each other at a position of the first actuator placed on the pair of the optical substrates and a distance between the surfaces of the pair of the optical substrates opposite to each other at a position of the second actuator placed on the pair of the optical substrate, with signals from the first and second capacitive sensors, the control unit actuating the first and third actuators on the basis of the distance between the centers of mass of the surfaces of the optical substrates, the first angle, and the difference between the distance between the surfaces of the pair of the optical substrates opposite to each other at the placed position of the first actuator and the distance between the surfaces of the pair of the optical substrates opposite to each other at the placed position of the second actuator, the control unit actuating the second and fourth actuators on the basis of the distance between the centers of mass of the surfaces of the optical substrates, the second angle, and the difference between the distance between the surfaces of the pair of the optical substrates opposite to each other at the placed position of the first actuator and the distance between the surfaces of the pair of the optical substrates opposite to each other at the placed position of the second actuator, and the control unit repeating the process which ranges from the calculation of a distance between the centers of mass of the surfaces of the optical substrates to the actuations of the second and fourth actuators until the difference between the distance between the surfaces of the pair of the optical substrates opposite to each other at the placed position of the first actuator and the distance between the surfaces of the pair of the optical substrates opposite to each other at the placed position of the second actuator becomes approximately equal to zero.

2. A variable spectrum element according to claim 1, wherein the first, second, third, and fourth capacitive sensors and the first, second, third, and fourth actuators are placed at positions at which the first, second, third, and fourth capacitive sensors overlap with the first, second, third, and fourth actuators respectively when these capacitive sensors and these actuators are viewed from a direction along the line connecting the centers of mass of the surfaces of the pair of the optical substrates opposite to each other, respectively, and the following conditions are satisfied:

$$x_1 = x - r \sin \theta$$

$$x_2 = x - r \sin \phi$$

$$x_3 = x + r \sin \theta$$

$$x_4 = x + r \sin \phi$$

where x denotes a distance between the centers of mass of the surfaces of the pair of the optical substrates, $x_1$, $x_2$, $x_3$, and $x_4$ denote distances between the surfaces of the pair of the optical substrates opposite to each other at the positions at which the first, second, third, and fourth capacitive sensors are placed respectively, respectively, $\theta$ denotes the first angle, $\phi$ denotes the second angle, and r denotes a distance between the center of mass of the surface of the relatively moved optical substrate of the surfaces of the pair of the optical substrates opposite to each other and the position of each of the first to fourth capacitive sensors placed on the surface of the relatively moved optical substrate.

3. A variable spectrum element according to claim 1, wherein the control unit calculates a distance between the centers of mass of the surfaces of the optical substrates, with the average of distances between the surfaces of the pair of the optical substrates opposite to each other at the positions at which the first, second, third, and fourth capacitive sensors are placed respectively, the control unit calculates the first angle, with a difference between distances between the surfaces of the pair of the optical substrates opposite to each other at the positions at which the first and third capacitive sensors are placed respectively, the control unit calculates the second angle, with a difference between distances between the surfaces of the pair of the optical substrates opposite to each other at the positions at which the second and fourth capacitive sensors are placed respectively, and the control unit calculates a difference between the distance between the surfaces of the pair of the optical substrates opposite to each other at the placed position of the first actuator and the distance between the surfaces of the pair of the optical substrates opposite to each other at the placed position of the second actuator, with a difference between a distance between the surfaces of the pair of the optical substrates opposite to each other at the position of the first capacitive sensor placed and a distance between the surfaces of the pair of the optical substrates opposite to each other at the position of the second capacitive sensor placed.

4. A variable spectrum element according to claim 1, wherein the first, second, third, and fourth capacitive sensors and the first, second, third, and fourth actuators are placed at positions at which the first, second, third, and fourth capacitive sensors overlap with the first, second, third, and fourth actuators respectively when these capacitive sensors and these actuators are viewed from a direction along the line connecting the centers of mass of the surfaces of the pair of the optical substrates opposite to each other, respectively, and the following conditions are satisfied:

$$x = (x_1 + x_2 + x_3 + x_4)/4$$

$$\theta = R_1(x_3 - x_1)$$

$$\phi = R_2(x_4 - x_2)$$

where x denotes a distance between the centers of mass of the surfaces of pair of the optical substrates, $x_1$, $x_2$, $x_3$, and $x_4$ denote distances between the surfaces of the pair of the optical substrates opposite to each other at the positions at which the first, second, third, and fourth capacitive sensors are placed respectively, respectively, $\theta$ denotes the first angle, $\phi$ denotes the second angle, and $R_1$ and $R_2$ denote predetermined coefficients.

5. A variable spectrum element according to claim 1, comprising a property difference correction voltage applying unit by which an offset voltage for cancelling a difference between the properties of the first, second, third, and fourth actuators is applied to each of the first, second, third, and fourth actuators in operating the control unit.

6. A variable spectrum element comprising
a pair of optical substrates arranged opposite at a distance from each other,
first, second, third, and fourth capacitive sensors each including a pair of electrodes that are placed on surfaces of the pair of the optical substrates opposite to each other respectively and each detecting a distance between the surfaces of the pair of the optical substrates opposite to each other at each placed position, and
first, second, third, and fourth actuators relatively moving one of the pair of the optical substrates relative to the other optical substrate to change a distance between the surfaces of the pair of the optical substrates opposite to each other,
the first and third capacitive sensors being placed at positions at which the first and third capacitive sensors are symmetrical with respect to a line connecting centers of mass of the surfaces of the pair of the optical substrates opposite to each other, respectively,
the second and fourth capacitive sensors being placed at positions at which the second and fourth capacitive sensors are symmetrical with respect to the line connecting the centers of mass of the surfaces of the pair of the optical substrates opposite to each other, respectively,
the first, second, third, and fourth capacitive sensors and the first, second, third, and fourth actuators being placed on a circle at regular intervals one after the other when these capacitive sensors and these actuators are viewed from a direction along the line connecting the centers of mass of the surfaces of the pair of the optical substrates opposite to each other, and
the variable spectrum element comprising a control unit,
the control unit calculating a distance between the centers of mass of the surfaces of the pair of the optical substrates opposite to each other, with signals from the first, second, third, and fourth capacitive sensors,
the control unit calculating distances between the surfaces of the pair of the optical substrates opposite to each other at positions of the first, second, third, and fourth actuators placed on the pair of the optical substrates respectively, with signals from the first, second, third, and fourth capacitive sensors,
the control unit calculating a first angle that is made between a surface perpendicular to the line connecting the centers of mass of the surfaces of the pair of the optical substrates and the surface of the relatively moved optical substrate of the surfaces of the pair of the optical substrates opposite to each other, with the values of the distances between the surfaces of the pair of the optical substrates opposite to each other at the placed positions of the first and third actuators,
the control unit calculating a second angle that is made between the surface perpendicular to the line connecting the centers of mass of the surfaces of the pair of the optical substrates and the surface of the relatively moved optical substrate of the surfaces of the pair of the optical substrates opposite to each other, with the values of the distances between the surfaces of the pair of the optical substrates opposite to each other at the placed positions of the second and fourth actuators,
the control unit actuating the first and third actuators on the basis of the distance between the centers of mass of the surfaces of the optical substrates, the first angle, and a difference between the distance between the surfaces of the pair of the optical substrates opposite to each other at the placed position of the first actuator and the distance between the surfaces of the pair of the optical substrates opposite to each other at the placed position of the second actuator,
the control unit actuating the second and fourth actuators on the basis of the distance between the centers of mass of the surfaces of the optical substrates, the second angle, and the difference between the distance between the surfaces of the pair of the optical substrates opposite to each other at the placed position of the first actuator and the distance between the surfaces of the pair of the optical substrates opposite to each other at the placed position of the second actuator, and
the control unit repeating the process which ranges from the calculation of a distance between the centers of mass of the surfaces of the optical substrates to the actuations of the second and fourth actuators until the difference between the distance between the surfaces of the pair of the optical substrates opposite to each other at the placed position of the first actuator and the distance between the surfaces of the pair of the optical substrates opposite to each other at the placed position of the second actuator becomes approximately equal to zero.

7. A variable spectrum element according to claim 6, comprising a property difference correction voltage applying unit by which an offset voltage for cancelling a difference between the properties of the first, second, third, and fourth actuators is applied to each of the first, second, third, and fourth actuators in operating the control unit.

8. A variable spectrum element comprising
a pair of optical substrates arranged opposite at a distance from each other,
first, second, third, and fourth capacitive sensors each including a pair of electrodes that are placed on surfaces of the pair of the optical substrates opposite to each other respectively and each detecting a distance between the surfaces of the pair of the optical substrates opposite to each other at each placed position, and
first, second, third, and fourth actuators relatively moving one of the pair of the optical substrates relative to the other optical substrate to change a distance between the surfaces of the pair of the optical substrates opposite to each other,
the first and third capacitive sensors being placed at positions at which the first and third capacitive sensors are symmetrical with respect to a line connecting centers of mass of the surfaces of the pair of the optical substrates opposite to each other, respectively, the second and fourth capacitive sensors being placed at positions at which the second and fourth capacitive sensors are symmetrical with respect to the line connecting the centers of mass of the surfaces of the pair of the optical substrates opposite to each other, respectively, the first, second, third, and fourth actuators being placed on lines running from the center of mass of the surface of each of the pair of the optical substrates opposite to each other to the centers of the first, second, third, and fourth capacitive sensors respectively, respectively, and the variable spectrum element comprising a control unit, the control unit calculating a distance between the centers of mass of the surfaces of the pair of the optical substrates opposite to each other, with signals from the first, second, third, and fourth capacitive sensors, the control unit calculating a first angle that is made between a surface perpendicular to the line connecting the centers of mass of the surfaces of the pair of the optical substrates and the surface of the relatively moved optical substrate of the surfaces of the pair of the optical substrates opposite to each other, with signals from the first and third capacitive sensors, the control unit calculating a second angle that is made between the surface perpendicular to the line connecting the centers of mass of the surfaces of the pair of the optical substrates and the surface of the relatively moved optical substrate of the surfaces of the pair of the optical substrates opposite to each other, with signals from the second and fourth capacitive sensors, the control unit calculating the average of the first directional surface distances that is obtained by taking the average of a distance between the surfaces of the pair of the optical substrates opposite to each other at a position of the first actuator placed on the pairs of the optical substrates and a distance between the surfaces of the pair of the optical substrates opposite to each other at a position of the third actuator placed on the pairs of the optical substrates, with signals from the first and third capacitive sensors, the control unit calculating the average of the second directional surface distances that is obtained by taking the average of a distance between the surfaces of the pair of the optical substrates opposite to each other at a position of the second actuator placed on the pair of the optical substrates and a distance between the surfaces of the pair of the optical substrates opposite to each other at a position of the fourth actuator placed on the pair of the optical substrates, with signals from the second and fourth capacitive sensors, the control unit calculating a difference between the average of the first directional surface distances and the average of the second directional surface distances, the control unit actuating the first and third actuators on the basis of the distance between the centers of mass of the surfaces of the optical substrates, the first angle, and the difference between the average of the first directional surface distances and the average of the second directional surface distances, the control unit actuating the second and fourth actuators on the basis of the distance between the centers of mass of the surfaces of the optical substrates, the second angle, and the difference between the average of the first directional surface distances and the average of the second directional surface distances, and the control unit repeating the process which ranges from the calculation of a distance between the centers of mass of the surfaces of the optical substrates to the actuations of the second and fourth actuators until the difference between the average of the first directional surface distances and the average of the second directional surface distances becomes approximately equal to zero.

9. A variable spectrum element according to claim 8, wherein the first, second, third, and fourth capacitive sensors and the first, second, third, and fourth actuators are placed at positions at which the first, second, third, and fourth capacitive sensors overlap with the first, second, third, and fourth actuators respectively when these capacitive sensors and these actuators are viewed from a direction along the line connecting the centers of mass of the surfaces of the pair of the optical substrates opposite to each other, respectively, and the following conditions are satisfied:

$$x_1 = x - r \sin \theta$$

$$x_2 = x - r \sin \phi$$

$$x_3 = x + r \sin \theta$$

$$x_4 = x + r \sin \phi$$

where x denotes a distance between the centers of mass of the surfaces of the pair of the optical substrates, $x_1$, $x_2$, $x_3$, and $x_4$ denote distances between the surfaces of the pair of the optical substrates opposite to each other at the positions at which the first, second, third, and fourth capacitive sensors are placed respectively, respectively, $\theta$ denotes the first angle, $\phi$ denotes the second angle, and r denotes a distance between the center of mass of the surface of the relatively moved optical substrate of the surfaces of the pair of the optical substrates opposite to each other and the position of each of the first to fourth capacitive sensors placed on the surface of the relatively moved optical substrate.

10. A variable spectrum element according to claim 8, wherein the control unit calculates a distance between the centers of mass of the surfaces of the optical substrates, with the average of distances between the surfaces of the pair of the optical substrates opposite to each other at the positions at which the first, second, third, and fourth capacitive sensors are placed respectively, the control unit calculates the first angle, with a difference between distances between the surfaces of the pair of the optical substrates opposite to each other at the positions at which the first and third capacitive sensors are placed respectively, the control unit calculates the second angle, with a difference between distances between the surfaces of the pair of the optical substrates opposite to each other at the positions at which the second and fourth capacitive sensors are placed respectively, and the control unit calculates a difference between the average of the first directional surface distances and the average of the second directional surface distances, by calculating a difference between the average of the distance between the surfaces of the pair of the optical substrates opposite to each other at the position of the first capacitive sensor placed and the distance between the surfaces of the pair of the optical substrates opposite to each other at the position of the third capacitive sensor placed and the average of the distance between the surfaces of the pair of the optical substrates opposite to each other at the position of the second capacitive sensor placed and the distance between the surfaces of the pair of the optical substrates opposite to each other at the position of the fourth capacitive sensor placed.

11. A variable spectrum element according to claim 8, wherein the first, second, third, and fourth capacitive sensors and the first, second, third, and fourth actuators are placed at positions at which the first, second, third, and fourth capacitive sensors overlap with the first, second, third, and fourth actuators respectively when these capacitive sensors and these actuators are viewed from a direction along the line connecting the centers of mass of the surfaces of the pair of the optical substrates opposite to each other, respectively, and the following conditions are satisfied:

$$x=(x_1+x_2+x_3+x_4)/4$$

$$\theta=R_1(x_3-x_1)$$

$$\phi=R_2(x_4-x_2)$$

where x denotes a distance between the centers of mass of the surfaces of pair of the optical substrates, $x_1$, $x_2$, $x_3$, and $x_4$ denote distances between the surfaces of the pair of the optical substrates opposite to each other at the positions at which the first, second, third, and fourth capacitive sensors are placed respectively, respectively, $\theta$ denotes the first angle, $\phi$ denotes the second angle, and $R_1$ and $R_2$ denote predetermined coefficients.

12. A variable spectrum element according to claim 8, comprising a property difference correction voltage applying unit by which an offset voltage for cancelling a difference between the properties of the first, second, third, and fourth actuators is applied to each of the first, second, third, and fourth actuators in operating the control unit.

13. A variable spectrum element comprising
a pair of optical substrates arranged opposite at a distance from each other,
first, second, third, and fourth capacitive sensors each including a pair of electrodes that are placed on surfaces of the pair of the optical substrates opposite to each other respectively and each detecting a distance between the surfaces of the pair of the optical substrates opposite to each other at each placed position, and
first, second, third, and fourth actuators relatively moving one of the pair of the optical substrates relative to the other optical substrate to change a distance between the surfaces of the pair of the optical substrates opposite to each other,
the first and third capacitive sensors being placed at positions at which the first and third capacitive sensors are symmetrical with respect to a line connecting centers of mass of the surfaces of the pair of the optical substrates opposite to each other, respectively,
the second and fourth capacitive sensors being placed at positions at which the second and fourth capacitive sensors are symmetrical with respect to the line connecting the centers of mass of the surfaces of the pair of the optical substrates opposite to each other, respectively,
the first, second, third, and fourth capacitive sensors and the first, second, third, and fourth actuators being placed on a circle at regular intervals one after the other when these capacitive sensors and these actuators are viewed from a direction along the line connecting the centers of mass of the surfaces of the pair of the optical substrates opposite to each other, and
the variable spectrum element comprising a control unit,
the control unit calculating a distance between the centers of mass of the surfaces of the pair of the optical substrates opposite to each other, with signals from the first, second, third, and fourth capacitive sensors,
the control unit calculating distances between the surfaces of the pair of the optical substrates opposite to each other at positions of the first, second, third, and fourth actuators placed on the pair of the optical substrates respectively, with signals from the first, second, third, and fourth capacitive sensors,
the control unit calculating the average of the first directional surface distances that is obtained by taking the average of the distances between the surfaces of the pair of the optical substrates opposite to each other at the positions of the first and third actuators placed on the pair of the optical substrates respectively and calculating the average of the second directional surface distances that is obtained by taking the average of the distances between the surfaces of the pair of the optical substrates opposite to each other at the positions of the second and fourth actuators placed on the pair of the optical substrates respectively,
the control unit calculating a first angle that is made between a surface perpendicular to the line connecting the centers of mass of the surfaces of the pair of the optical substrates and the surface of the relatively moved optical substrate of the surfaces of the pair of the optical substrates opposite to each other, with the values of the distances between the surfaces of the pair of the optical substrates opposite to each other at the placed positions of the first and third actuators,
the control unit calculating a second angle that is made between the surface perpendicular to the line connecting the centers of mass of the surfaces of the pair of the optical substrates and the surface of the relatively moved optical substrate of the surfaces of the pair of the optical substrates opposite to each other, with the values of the distances between the surfaces of the pair of the optical substrates opposite to each other at the placed positions of the second and fourth actuators,
the control unit actuating the first and third actuators on the basis of the distance between the centers of mass of the surfaces of the optical substrates, the first angle, and a difference between the average of the first directional surface distances and the average of the second directional surface distances,
the control unit actuating the second and fourth actuators on the basis of the distance between the centers of mass of the surfaces of the optical substrates, the second angle, and the difference between the average of the first directional surface distances and the average of the second directional surface distances, and
the control unit repeating the process which ranges from the calculation of a distance between the centers of mass of the surfaces of the optical substrates to the actuations of the second and fourth actuators until the difference between the average of the first directional surface distances and the average of the second directional surface distances becomes approximately equal to zero.

14. A variable spectrum element according to claim 13, comprising a property difference correction voltage applying unit by which an offset voltage for cancelling a difference between the properties of the first, second, third, and fourth actuators is applied to each of the first, second, third, and fourth actuators in operating the control unit.

* * * * *